United States Patent
Duffy et al.

(10) Patent No.: US 7,273,876 B2
(45) Date of Patent: Sep. 25, 2007

(54) SUBSTITUTED BICYLIC THIOPHENE DERIVATIVES, COMPOSITIONS CONTAINING SUCH COMPOUNDS AND METHODS OF USE

(75) Inventors: Joseph Duffy, Cranford, NJ (US); Elizabeth Louise Campbell, North Brunswick, NJ (US); Rui Liang, East Brunswick, NJ (US); Zenon Konteatis, Chatham Township, NJ (US)

(73) Assignee: Merck & Co., Inc., Rahway, NJ (US)

( * ) Notice: Subject to any disclaimer, the term of this patent is extended or adjusted under 35 U.S.C. 154(b) by 273 days.

(21) Appl. No.: 10/527,762

(22) PCT Filed: Sep. 8, 2003

(86) PCT No.: PCT/US03/28033

§ 371 (c)(1),
(2), (4) Date: Mar. 11, 2005

(87) PCT Pub. No.: WO2004/024065

PCT Pub. Date: May 25, 2004

(65) Prior Publication Data

US 2005/0239865 A1    Oct. 27, 2005

Related U.S. Application Data

(60) Provisional application No. 60/410,145, filed on Sep. 12, 2002.

(51) Int. Cl.
*A61K 31/4365* (2006.01)
*A61K 31/381* (2006.01)
*C07D 495/04* (2006.01)

(52) U.S. Cl. ............... 514/301; 514/443; 546/114; 549/50

(58) Field of Classification Search ........... 514/301, 514/443; 546/114; 549/50
See application file for complete search history.

(56) References Cited

OTHER PUBLICATIONS

Fujita et al. "Synthesis and Bioactivities of Novel Bicylic Thiophenes and 4,5,6,7-Tetrahydrothieno[2,3-c]pyridines as Inhibitors of Tumor Necrosis Factor-a (TNF-a) Production" Bioorganic and Medicinal Chemistry Letters, 2002, vol. 12, pp. 1897-1900.*
Fujita, et al—Database Cas Online on STN, Chem. Abstra., Accession No. 2002:510557, 2002.
Fujita, M. et al., "Snthesis and Bioactivities of Novel Bicylic Thiophenes and 4,5,6,7-Tetrahydrothienol[2,3-c]pyridines as Inhibitors of Tumor Necrosis Factor-alpha (TNF-alpha) Production" Bioorganic & Medicinal Chemistry Letters, vol. 12, pp. 1897-1900, 2002.

* cited by examiner

*Primary Examiner*—Rebecca Anderson
*Assistant Examiner*—Joseph R. Kosack
(74) *Attorney, Agent, or Firm*—Richard C. Billups; Catherine D. Fitch

(57) ABSTRACT

The present invention addresses substituted thiophene derivatives, as well as compositions containing such compounds and methods of treatment. The compounds in the present invention are glucagon antagonists. The compounds block the action of glucagon at its receptor and thereby decrease the levels of plasma glucose providing a treatment of diabetes.

10 Claims, No Drawings

SUBSTITUTED BICYLIC THIOPHENE DERIVATIVES, COMPOSITIONS CONTAINING SUCH COMPOUNDS AND METHODS OF USE

CROSS REFERENCE TO RELATED APPLICATIONS

This application is the National Stage of International Application No. PCT/US03/28033, filed 8 Sep. 2003, which claims the benefit under 35 U.S.C. 119(e) of U.S. Provisional Application No. 60/410,145, filed 12 Sept. 2002.

BACKGROUND OF THE INVENTION

The present invention relates to substituted thiophene derivatives, compositions containing such compounds and methods of treating type 2 diabetes mellitus.

Diabetes refers to a disease process derived from multiple causative factors and is characterized by elevated levels of plasma glucose (hyperglycemia) in the fasting state or following glucose administration during an oral glucose tolerance test. Frank diabetes mellitus (e.g., a blood glucose level $\geq 126$ mg/dL in a fasting state) is associated with increased and premature cardiovascular morbidity and mortality, and is related directly and indirectly to various metabolic conditions, including alterations of lipid, lipoprotein and apolipoprotein metabolism.

Patients with non-insulin dependent diabetes mellitus (type 2 diabetes mellitus), approximately 95% of patients with diabetes mellitus, frequently display elevated levels of serum lipids, such as cholesterol and triglycerides, and have poor blood-lipid profiles, with high levels of LDL-cholesterol and low levels of HDL-cholesterol. Those suffering from Type 2 diabetes mellitus are thus at an increased risk of developing macrovascular and microvascular complications, including coronary heart disease, stroke, peripheral vascular disease, hypertension (for example, blood pressure $\geq 130/80$ mmHg in a resting state), nephropathy, neuropathy and retinopathy.

Patients having type 2 diabetes mellitus characteristically exhibit elevated plasma insulin levels compared with non-diabetic patients; these patients have developed a resistance to insulin stimulation of glucose and lipid metabolism in the main insulin-sensitive tissues (muscle, liver and adipose tissues). Thus, Type 2 diabetes, at least early in the natural progression of the disease is characterized primarily by insulin resistance rather than by a decrease in insulin production, resulting in insufficient uptake, oxidation and storage of glucose in muscle, inadequate repression of lipolysis in adipose tissue, and excess glucose-production and secretion by the liver. The net effect of decreased sensitivity to insulin is high levels of insulin circulating in the blood without appropriate reduction in plasma glucose (hyperglycemia). Hyperinsulinemia is a risk factor for developing hypertension and may also contribute to vascular disease.

Glucagon serves as the major regulatory hormone attenuating the effect of insulin in its inhibition of liver gluconeogenesis and is normally secreted by α-cells in pancreatic islets in response to falling blood glucose levels. The hormone binds to specific receptors in liver cells that triggers glycogenolysis and an increase in gluconeogenesis through cAM-mediated events. These responses generate glucose (e.g. hepatic glucose production) to help maintain euglycemia by preventing blood glucose levels from falling significantly.

In addition to elevated levels of circulating insulin, type II diabetics have elevated levels of plasma glucagon and increased rates of hepatic glucose production. Antagonists of glucagon are useful in improving insulin responsiveness in the liver, decreasing the rate of gluconeogenesis and lowering the rate of hepatic glucose output resulting in a decrease in the levels of plasma glucose.

SUMMARY OF INVENTION

The present invention is directed to a compound represented by formula I:

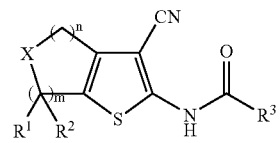

or a pharmaceutically acceptable salt or solvate thereof wherein:

X is $NR^4$ or $CR^5R^6$;

$R^1$ is selected from the group consisting of: H, $C_{1-10}$alkyl, $C_{3-7}$cycloalkyl and Aryl, said alkyl, cycloalkyl and Aryl being optionally substituted with 1-4 substituents independently selected from $R^{13}$;

$R^2$ is selected from the group consisting of: $R^1$ as defined above, $-C(O)_2R^7$ and $-CONR^7R^8$;

m and n are selected from 0, 1, 2 and 3, such that the sum of m and n is 2 or 3, and when m is greater than 1, no more than one $R^1$ and no more than one $R^2$ can be other than H;

$R^3$ is selected from the group consisting of: $C_{1-10}$alkyl, $C_{3-7}$cycloalkyl and Aryl, said alkyl, cycloalkyl and Aryl being optionally substituted with 14 substituents selected from $R^{13}$, such that when $R^3$ represents $C_{1-10}$ alkyl substituted with one $R^{13}$ group, and $R^{13}$ represents halo, $R^1$, $R^2$, $R^5$ and $R^6$ do not represent $C_{1-3}$alkyl;

$R^4$ is selected from the group consisting of: $C_{3-10}$ alkyl, $C_{3-7}$ cycloalkyl, Aryl, HAR, Hetcy, $C(O)C_{5-10}$ alkyl, $C(O)$ $C_{3-7}$ cycloalkyl, $C(O)$-Aryl, $C(O)$—HAR, $C(O)$-Hetcy, $CONR^9R^{10}$, $CO_2R^9$ and $SO_2R^9$, the alkyl, cycloalkyl, Aryl, HAR and Hetcy groups and portions being optionally substituted with 1-4 substituents selected from $R^{13}$;

one of $R^5$ and $R^6$ is selected from the group consisting of $NR^{11}R^{12}$, $NR^{11}CORR^{12}$, $NR^{11}CO_2R^{12}$ and $NR^{11}S(O)_2R^{12}$, and the other represents $R^1$, HAR, Hetcy or $OR^{11}$, said HAR and Hetcy being optionally substituted with 1-4 substituents selected from $R^{13}$, $R^7$, $R^{10}$ and $R^{11}$ are selected from the group consisting of: $R^1$ as defined above, HAR and Hetcy, said HAR and Hetcy being optionally substituted with 1-4 substituents selected from $R^{13}$;

$R^8$, $R^9$ and $R^{12}$ are selected from the group consisting of: $C_{1-10}$alkyl, $C_{3-7}$cycloalkyl, Aryl, HAR and Hetcy, said alkyl, cycloalkyl, Aryl, HAR and Hetcy being optionally substituted with 1-4 substituents selected from $R^{13}$;

or alternatively, $R^7$, $R^8$, $R^9$ and $R^{10}$ are as defined above, and $R^{11}$ and $R^{12}$ are taken together with the atoms to which they are attached along with any intervening atoms and represent a 5-8 membered ring optionally containing 1-2 heteroatoms selected from O, S and N, and optionally substituted with 14 substituents selected from $R^{13}$;

each $R^{13}$ is selected from the group consisting of: halo, $NR^{14}R^{15}$, $C_{1-4}$alkyl, $C_{3-7}$ cycloalkyl, Aryl, HAR, Hetcy, $CF_3$, $OCF_3$, $OR^{15}$, $NO_2$, $S(O)_xR^{14}$, $SR^{14}$, $S(O)_xNR^{14}R^{15}$, $O(CR^{16}R^{17})_yNR^{14}R^{15}$, $C(O)R^{14}$, $CO_2R^{15}$, $CO_2(CR^{16}R^{17})_y$, $CONR^{14}R^{15}$, $OC(O)R^{14}$, $CN$, $C(O)NR^{14}R^{15}$, $NR^{15}C(O)R^{14}$, $NR^{15}C(O)OR^{14}$, $NR^{15}C(O)NR^{16}R^{14}$ and $CR^{15}(N-OR^{14})$, wherein x is 1 or 2, and y is an integer from 1-4, said alkyl, cycloalkyl, Aryl, HAR and Hetcy being optionally substituted with 1-4 substituents selected from $R^{18}$;

$R^{14}$, $R^{15}$, $R^{16}$ and $R^{17}$ are independently selected from the group consisting of: H, $C_{1-10}$alkyl, $C_{3-7}$cycloalkyl, Aryl and Ar—$C_{1-10}$alkyl;

and each $R^{18}$ is independently selected from the group consisting of: halogen, CN, $C_{1-4}$alkyl, OH, $CF_3$, Aryl, Aryloxy, $CO_2H$ and $CO_2C_{1-4}$ alkyl, said Aryl and the Aryl portion of Aryloxy being optionally substituted with up to 4 halo groups, and up to 2 $C_{1-4}$ alkyl, OH, $CF_3$ or CN groups.

DETAILED DESCRIPTION OF THE INVENTION

The invention is described herein in detail using the terms defined below unless otherwise specified.

"Alkyl", as well as other groups having the prefix "alk", such as alkoxy, alkanoyl and the like, means carbon chains which may be linear, branched, or cyclic, or combinations thereof, containing the indicated number of carbon atoms. If no number is specified, 1-10 carbon atoms are intended for linear or branched alkyl groups. Examples of alkyl groups include methyl, ethyl, propyl, isopropyl, butyl, sec- and tert-butyl, pentyl, hexyl, heptyl, octyl, nonyl and the like. Cycloalkyl is a subset of alkyl; if no number of atoms is specified, 3-10 carbon atoms are intended, forming 1-3 carbocyclic rings that are fused. "Cycloalkyl" also includes monocyclic rings fused to an aryl group in which the point of attachment is on the non-aromatic portion. Examples of cycloalkyl include cyclopropyl, cyclobutyl, cyclopentyl, cyclohexyl, cycloheptyl, tetrahydronaphthyl, decahydronaphthyl, indanyl and the like.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Aryl" (Ar) means mono- and bicyclic aromatic rings containing only carbon atoms. Examples of aryl include phenyl and naphthyl.

"Heteroaryl" (HAR) means a mono- or bicyclic aromatic ring or ring system containing at least one heteroatom selected from O, S and N, with each ring containing 5 to 6 atoms. Examples include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, furo(2,3-b)pyridyl, quinolyl, indolyl, isoquinolyl and the like. Heteroaryl also includes aromatic heterocyclic groups fused to heterocycles that are non-aromatic or partially aromatic, and aromatic heterocyclic groups fused to cycloalkyl rings.

"Heterocyclyl" (Hetcy) means mono- and bicyclic saturated rings and ring systems containing at least one heteroatom selected from N, S and O, each of said ring having from 3 to 10 atoms in which the point of attachment may be carbon or nitrogen. Examples of "heterocyclyl" include pyrrolidinyl, piperidinyl, piperazinyl, imidazolidinyl, 2,3-dihydrofuro(2,3-b)pyridyl, benzoxazinyl, tetrahydrohydroquinolinyl, tetrahydroisoquinolinyl, dihydroindolyl, and the like. The term also includes partially unsaturated monocyclic rings that are not aromatic, such as 2- or 4-pyridones attached through the nitrogen or N-substituted-(1H,3H)-pyrimidine-2,4-diones (N-substituted uracils).

"Halogen" (Halo) includes fluorine, chlorine, bromine and iodine.

The present invention is directed to a compound represented by formula I:

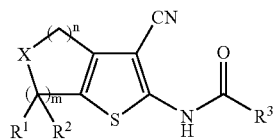

or a pharmaceutically acceptable salt or solvate thereof wherein:

X is $NR^4$ or $CR^5R^6$;

$R^1$ is selected from the group consisting of: H, $C_{1-10}$alkyl, $C_{3-7}$cycloalkyl and Aryl, said alkyl, cycloalkyl and Aryl being optionally substituted with 1-4 substituents independently selected from $R^{13}$;

$R^2$ is selected from the group consisting of: $R^1$ as defined above, —$C(O)_2R^7$ and —$CONR^7R^8$;

m and n are selected from 0, 1, 2 and 3, such that the sum of m and n is 2 or 3, and when m is greater than 1, no more than one $R^1$ and no more than one $R^2$ can be other than H;

$R^3$ is selected from the group consisting of: $C_{1-10}$alkyl, $C_{3-7}$cycloalkyl and Aryl, said alkyl, cycloalkyl and Aryl being optionally substituted with 1-4 substituents selected from $R^{13}$, such that when $R^3$ represents $C_{1-10}$alkyl substituted with one $R^{13}$ group, and $R^{13}$ represents halo, $R^1$, $R^2$, $R^5$ and $R^6$ do not represent $C_{1-3}$alkyl;

$R^4$ is selected from the group consisting of: $C_{3-10}$ alky, $C_{3-7}$ cycloalkyl, Aryl, HAR, HetCy, $C(O)C_{5-10}$ alkyl, $C(O)$ $C_{3-7}$ cycloalkyl, $C(O)$-Aryl, $C(O)$—HAR, $C(O)$-Hetcy, $CONR^9R^{10}$, $CO_2R^9$ and $SO_2R^9$, the alkyl, cycloalkyl, Aryl, HAR and Hetcy groups and portions being optionally substituted with 14 substituents selected from $R^{13}$;

one of $R^5$ and $R^6$ is selected from the group consisting of $NR^{11}R^{12}$, $NR^{11}COR^{12}$, $N^{11}CO_2R^{12}$ and $NR^{11}S(O)_2R^{12}$, and the other represents $R^1$, HAR, Hetcy or $OR^{11}$, said HAR and Hetcy being optionally substituted with 14 substituents selected from $R^{13}$, $R^7$, $R^{10}$ and $R^{11}$ are selected from the group consisting of: $R^1$ as defined above, HAR and Hetcy, said HAR and Hetcy being optionally substituted with 14 substituents selected from $R^{13}$;

$R^8$, $R^9$ and $R^{12}$ are selected from the group consisting of: $C_{1-10}$alkyl, $C_{3-7}$cycloalkyl, Aryl, HAR and Hetcy, said alkyl, cycloalkyl, Aryl, HAR and Hetcy being optionally substituted with 1-4 substituents selected from $R^{13}$;

or alternatively, $R^7$, $R^8$, $R^9$ and $R^{10}$ are as defined above, and $R^{11}$ and $R^{12}$ are taken together with the atoms to which they are attached along with any intervening atoms and represent a 5-8 membered ring optionally containing 1-2 heteroatoms selected from O, S and N, and optionally substituted with 14 substituents selected from $R^{13}$;

each $R^{13}$ is selected from the group consisting of: halo, $NR^{14}R^{15}$, $C_{14}$alkyl, $C_{3-7}$ cycloalkyl, Aryl, HAR, Hetcy, $CF_3$, $OCF_3$, $OR^{15}$, $NO_2$, $S(O)_xR^{14}$, $SR^{14}$, $S(O)_xNR^{14}R^{15}$, $O(CR^{16}R^{17})_x NR^{14}R^{15}$, $C(O)R^{14}$, $CO_2R^{15}$, $CO_2(CR^{16}R^{17})_y$ $CONR^{14}R^{15}$) $OC(O)R^{14}$, $CN$, $C(O)NR^{14}R^{15}$, $NR^{15}C(O)R^{14}$, $NR^{15}C(O)OR^{14}$, $NR^{15}C(O)NR^{16}R^{14}$ and $CR^{15}(N\text{—}OR^{14})$, wherein x is 1 or 2, and y is an integer from 1-4, said alkyl, cycloalkyl, Aryl, HAR and Hetcy being optionally substituted with 1-4 substituents selected from $R^{18}$;

$R^{14}$, $R^{15}$, $R^{16}$ and $R^{17}$ are independently selected from the group consisting of: H, $C_{1-10}$alkyl, $C_{3-7}$cycloalkyl, Aryl and Ar—$C_{1-10}$alkyl;

and each $R^{18}$ is independently selected from the group consisting of: halogen, CN, $C_{1-4}$alkyl, OH, $CF_3$, Aryl, Aryloxy, $CO_2H$ and $CO_2C_{1-4}$ alkyl, said Aryl and the Aryl portion of Aryloxy being optionally substituted with up to 4 halo groups, and up to 2 $C_{1-4}$ alkyl, OH, $CF_3$ or CN groups.

In an aspect of the invention that is of particular interest, a compound of formula I is disclosed wherein $R^1$ is selected from the group consisting of: H, $C_{1-10}$alkyl, $C_{3-4}$ cycloalkyl and phenyl, said alkyl and phenyl being optionally substituted with 1-3 substituents selected from $R^{13}$. Within this aspect of the invention, all other variables are as originally defined.

In another aspect of the invention that is of particular interest, a compound of formula I is disclosed wherein $R^2$ is H. Within this aspect of the invention, all other variables are as originally defined.

In another aspect of the invention that is of particular interest, a compound of formula I is disclosed wherein m is 0 and n is 2 or 3, or m is 1 and n is 1 or 2. Thus, the sum of m and n is 2 or 3. Within this aspect of the invention, all other variables are as originally defined.

In another aspect of the invention that is of particular interest, a compound of formula I is disclosed wherein $R^3$ is $C_{3-10}$ alkyl optionally substituted with 1-4 substituents selected from R such that when $R^3$ is substituted with one $R^{13}$ group, and $R^{13}$ represents halo, $R^1$, $R^2$, $R^5$ and $R^6$ do not represent $C_{1-3}$alkyl. Within this aspect of the invention, all other variables are as originally defined.

More particularly, an aspect of the invention that is of particular interest relates to a compound of formula I wherein $R^3$ represents $C_{3-5}$ alkyl, optionally substituted with 1-4 $R^{13}$ groups. Within this aspect of the invention, all other variables are as originally defined.

In another aspect of the invention that is of particular interest, a compound of formula I is disclosed wherein $R^4$ is selected from the group consisting of: $C_{5-10}$ alkyl, $C_{3-6}$cycloalkyl, phenyl, HAR, Hetcy, $C(O)C_{5-10}$alkyl, $C(O)C_{3-6}$ cycloalkyl and $CO_2R^9$, the alkyl, cycloalkyl and, Aryl groups and portions, phenyl, HAR and Hetcy being optionally substituted with 1-4 substituents selected from $R^{13}$, and $R^9$ representing $C_{1-10}$alkyl, $C_{3-7}$cycloalkyl, Aryl, HAR or Hetcy, said alkyl, cycloalkyl, Aryl groups and portions, HAR and Hetcy being optionally substituted with 1-4 $R^{13}$ groups. Within this aspect of the invention, all other variables are as originally defined.

In another aspect of the invention that is of particular interest, a compound of formula I is disclosed wherein X represents $CR^5R^6$, $R^5$ is $NR^{11}R^{12}$, and $R^6$ is selected from the group consisting of: $R^1$, HAR, Hetcy and $OR^{11}$, wherein $R^1$ is as originally defined, $R^{11}$ is $R^1$ or HAR, and $R^{12}$ is $C_{1-6}$alkyl, Aryl or HAR, said Aryl and HAR being optionally substituted with 1-4 $R^{13}$ groups, or $R^{11}$ and $R^{12}$ are taken in combination with the atom to which they are attached and represent a 5-6 membered ring optionally substituted with 1-2 $R^{13}$ groups. Within this aspect of the invention, all other variables are as originally defined.

In another aspect of the invention, a compound of formula I is disclosed wherein $R^{13}$ is selected from the group consisting of: halo, $C_{1-4}$alkyl, $C_{3-7}$cycloalkyl, Aryl, HAR, Hetcy, and $OR^{15}$ wherein $R^{15}$ is H, said alkyl, cycloalkyl, Aryl, HAR and Hetcy being optionally substituted with 1-4 substituents selected from $R^{18}$ and $R^{18}$ is halo, $C_{1-4}$alkyl, Aryl or $CO_2C_{1-4}$ alkyl.

Within this aspect of the invention, all other variables are as originally defined.

In yet another aspect of the invention that is of particular interest, a compound of formula I is disclosed wherein:

$R^1$ is selected from the group consisting of: H, $C_{1-10}$alkyl, $C_{3-6}$ cycloalkyl and phenyl, said alkyl and phenyl being optionally substituted with 1-3 substituents selected from $R^{13}$;

$R^2$ is H;

m is 0 and n is 2 or 3, or m is 1 and n is 1 or 2, such that the sum of m and n is 2 or 3;

$R^3$ is $C_{3-10}$ alkyl optionally substituted with 1-4 substituents selected from $R^{13}$, such that when $R^3$ is substituted with one $R^{13}$ group, and $R^{13}$ represents halo, $R^1$, $R^2$, $R^5$ and $R^6$ do not represent $C_{1-3}$alkyl;

$R^4$ is selected from the group consisting of: $C_{5-10}$ alkyl, $C_{3-6}$ cycloalkyl, phenyl, HAR, Hetcy, $C(O)C_{5-10}$alkyl, $C(O)C_{3-6}$ cycloalkyl and $CO_2R^9$, the alkyl, cycloalkyl and, Aryl groups and portions, phenyl, HAR and Hetcy being optionally substituted with 1-4 substituents selected from $R^{13}$, and $R^9$ representing $C_{1-10}$alkyl, $C_{3-7}$cycloalkyl, Aryl, HAR or Hetcy, said alkyl, cycloalkyl, Aryl groups and portions, HAR and Hetcy being optionally substituted with 1-4 $R^{13}$ groups;

X represents $CR^5R^6$, $R^5$ is $NR^{11}R^{12}$, and $R^6$ is selected from the group consisting of: $R^1$, HAR, Hetcy and $OR^{11}$, wherein $R^1$ is as originally defined, $R^{11}$ is $R^1$ or HAR, and $R^{12}$ is $C_{1-6}$alkyl, Aryl or HAR, said Aryl and HAR being optionally substituted with 1-4 $R^{13}$ groups, or $R^{11}$ and $R^{12}$ are taken in combination with the atom to which they are attached and represent a 5-6 membered ring optionally substituted with 1-2 $R^{13}$ groups;

$R^{13}$ is selected from the group consisting of: halo, $C_{1-4}$alkyl, $C_{3-7}$cycloalkyl, Aryl, HAR, Hetcy, and $OR^{15}$ wherein $R^{15}$ is H, said alkyl, cycloalkyl, Aryl, HAR and Hetcy being optionally substituted with 1-4 substituents selected from $R^{18}$ and $R^{18}$ is halo, $C_{1-4}$alkyl, Aryl or $CO_2C_{1-4}$ alkyl.

Species falling within the scope of the present invention that are of particular interest include the following:

tert-butyl 3-cyano-2-[(2-ethylbutanoyl)amino]-5,6-dihydrothieno[2,3-b]pyridine-7(4H)-carboxylate;

N-(3-cyano-7-isobutyl4,5,6,7-tetrahydrothieno[2,3-b]pyridin-2-yl)-2-ethylbutanamide;

N-(3-cyano-7-isopropyl-4,5,6,7-tetrahydrothieno[2,3-b]pyridin-2-yl)-2-ethylbutanamide;

N-{6-[(4'-chloro-1,1'-biphenyl-4-yl)methyl]-3-cyano-4,5,6,7-tetrahydrothieno[2,3-c]pyridin-2-yl}-2-ethlylbutanamide;

N-[3-cyano-6-(4-phenoxybenzyl)-4,5,6,7-tetrahydrothieno[2,3-c]pyridin-2-yl]-2-ethylbutanamide;

N-{6-[4-(4-chlorophenoxy)benzyl]-3-cyano-4,5,6,7-tetrahydrothieno[2,3-c]pyridin-2-yl}-2-ethylbutanamide;

N-[3-cyano-6-(3-phenoxybenzyl)-4,5,6,7-tetrahydrothieno[2,3-c]pyridin-2-yl]-2-ethylbutanamide;

N-(3-cyano-6-{[1-(2,4-dichlorophenyl)cyclopropyl]carbonyl}4,5,6,7-tetrahydrothieno[2,3-c]pyridin-2-yl)-2-ethylbutanamide;

N-{3-cyano-6-[(2,4-dichlorobenzyl)amino]4,5,6,7-tetrahydro-1-benzothien-2-yl}-2-ethylbutanamide;

N-{3-cyano-6-[(cyclopropylmethyl)(2,4-dichlorobenzyl)amino]4,5,6,7-tetrahydro-1-benzothien-2-yl}-2-ethylbutanamide;

N-{3-cyano-6-[(2,4-dichlorobenzyl)(isopropyl)amino]4,5,6,7-tetrahydro-1-benzothien-2-yl}-2-ethylbutanamide;

N-{3-cyano-6-[(2,4-dichlorobenzyl)(isopentyl)amino]-4,5,6,7-tetrahydro-1-benzothien-2-yl}-2-ethylbutanamide;

N-{3-cyano-6-[(2,4-dichlorobenzyl)(3,3-dimethylbutyl)amino]4,5,6,7-tetrahydro-1-benzothien-2-yl}-2-ethylbutanamide;

N-{3-cyano-6-[(2,4-dichlorobenzyl)(isobutyl)amino]-4,5,6,7-tetrahydro-1-benzothien-2-yl}-2-ethylbutanamide;

N-{3-cyano-6-[(2,4-dichlorobenzyl)(2-ethylbutyl)amino]-4,5,6,7-tetrahydro-1-benzothien-2-yl}-2-ethylbutanamide;

N-(3-cyano-6-{(2,4-dichlorobenzyl)[(4,5-dimethyl-2-furyl)methyl]amino}-4,5,6,7-tetrahydro-1-benzothien-2-yl)-2-ethylbutanamide;

N-{3-cyano-6-[(2,4-dichlorobenzyl)(3-phenylpropyl)amino]-4,5,6,7-tetrahydro-1-benzothien-2-yl}-2-ethylbutanamide;

N-{6-[(1-benzofuran-2-ylmethyl)(2,4-dichlorobenzyl)amino]-3-cyano-4,5,6,7-tetrahydro-1-benzothien-2-yl}-2-ethylbutanamide;

N-{3-cyano-6-[(2,4-dichlorobenzyl)(3,3,3-trifluoropropyl)amino]-4,5,6,7-tetrahydro-1-benzothien-2-yl}-2-ethylbutanamide;

N-{3-cyano-6-[(2,4-dichlorobenzyl)(4-fluorobenzyl)amino)-4,5,6,7-tetrahydro-1-benzothien-2-yl}-2-ethylbutanamide;

N-{3-cyano-6-[(2,4-dichlorobenzyl)(tetrahydrofuran-2-ylmethyl)amino]-4,5,6,7-tetrahydro-1-benzothien-2-yl}-2-ethylbutanamide;

N-(3-cyano-6-{(2,4-dichlorobenzyl)[(5-methyl-2-furyl)methyl]amino}-4,5,6,7-tetrahydro-1-benzothien-2-yl)-2-ethylbutanamide;

tert-butyl (2S)-2-{[{3-cyano-2-[(2-ethylbutanoyl)amino]-4,5,6,7-tetrahydro-1-benzothien-6-yl}(2,4-dichlorobenzyl)amino]methyl}pyrrolidine-1-carboxylate;

N-{3-cyano-6-[(3,4-dichlorobenzyl)amino]-4,5,6,7-tetrahydro-1-benzothien-2-yl}-2-ethylbutanamide;

N-{3-cyano-6-[(3,4-dichlorobenzyl)(methyl)amino]-4,5,6,7-tetrahydro-1-benzothien-2-yl}-2-ethylbutanamide;

N-(3-cyano-6-{[(2-phenyl-1,3-thiazol-5-yl)methyl]amino}-4,5,6,7-tetrahydro-1-benzothien-2-yl)-2-ethylbutanamide;

N-(3-cyano-6-{methyl[(2-phenyl-1,3-thiazol-5-yl)methyl]amino}-4,5,6,7-tetrahydro-1-benzothien-2-yl)-2-ethylbutanamide;

N-(3-cyano-6-{[(2-phenyl-1,3-thiazol-4-yl)methyl]amino-4,5,6,7-tetrahydro-1-benzothien-2-yl}-2-ethylbutanamide;

N-(3-cyano-6-{methyl[(2-phenyl-1,3-thiazol-4-yl)methyl]amino}4,5,6,7-tetrahydro-1-benzothien-2-yl)-2-ethylbutanamide;

N-{3-cyano-6-(1,2,3,4-tetrahydronaphthalen-1-ylamino)-4,5,6,7-tetrahydro-1-benzothien-2-yl]-2-ethylbutanamide;

N-{3-cyano-6-[methyl(1,2,3,4-tetrahydronaphthalen-1-yl)amino]-4,5,6,7-tetrahydro-1-benzothien-2-yl}-2-ethylbutanamide;

N-{3-cyano-6-[(2,3-dihydro-1H-inden-1-ylmethyl)amino]}4,5,6,7-tetrahydrol-benzothien-2-yl}-2-ethylbutanamide;

N-{3-cyano-6-[(2,3-dihydro-1H-inden-1-ylmethyl)(methyl)amino]-4,5,6,7-tetrahydro-1-benzothien-2-yl}-2-ethylbutanamide;

N-{6-[(2-chlorobenzyl)amino]-3-cyano-4,5,6,7-tetrahydro-1-benzothien-2-yl}-2-ethylbutanamide N-{6-[(2-chlorobenzyl)(methyl)amino]-3-cyano-4,5,6,7-tetrahydro-1-benzothien-2-yl}-2-ethylbutanamide;

N-(6-{[1-(4-bromophenyl)ethyl]amino}-3-cyano-4,5,6,7-tetrahydro-1-benzothien-2-yl)-2-ethylbutanamide;

N-{6-[[1-(4-bromophenyl)ethyl](methyl)amino]-3-cyano-4,5,6,7-tetrahydro-1-benzothien-2-yl}-2-ethylbutanamide;

N-[3-cyano-6-(3-phenylpyrrolidin-1-yl)-4,5,6,7-tetrahydro-1-benzothien-2-yl]-2-ethylbutanamide;

N-[3-cyano-6-(4-phenylpiperazin-1-yl)-4,5,6,7-tetrahydro-1-benzothien-2-yl]-2-ethylbutanamide;

N-{3-cyano-2-[(2-ethylbutanoyl)amino]-4,5,6,7-tetrahydro-1-benzothien-6-yl}-N-(2,4-dichlorobenzyl)-3,3-dimethylbutanamide;

N-{3-cyano-2-[(2-ethylbutanoyl)amino]-4,5,6,7-tetrahydro-1-benzothien-6-yl}-N-[1-(hydroxymethyl)-2,2-dimethylpropyl)cyclopropanecarboxamide;

N-{3-cyano-2-[(2-ethylbutanoyl)amino]-4,5,6,7-tetrahydro-1-benzothien-6-yl}-N-[1-(hydroxymethyl)-2,2-dimethylpropyl]-3,3-dimethylbutanamide;

N-{3-cyano-2-[(2-ethylbutanoyl)amino]-4,5,6,7-tetrahydro-1-benzothien-6-yl}-N-[1-(hydroxymethyl)-2,2-dimethylpropyl]cyclopentanecarboxamide;

N-{3-cyano-2-[(2-ethylbutanoyl)amino]-4,5,6,7-tetrahydro-1-benzothien-6-yl}-N-[1-(hydroxymethyl)-2,2-dimethylpropyl]benzamide and N-{3-cyano-2-[(2-ethylbutanoyl)amino]4,5,6,7-tetrahydro-1-benzothien-6-yl}-N-[1-(hydroxymethyl)-2,2-dimethylpropyl]cyclohexanecarboxamide.

The invention further includes a pharmaceutical composition which is comprised of a compound of formula I in combination with a pharmaceutically acceptable carrier.

Also included is a method of treating type 2 diabetes mellitus in a mammalian patient in need of such treatement, comprising administering to said patient a compound of formula I in an amount that is effective to treat type 2 diabetes mellitus.

Also included is a method of preventing or delaying the onset of type 2 diabetes mellitus in a mammalian patient in need thereof, comprising administering to said patient a compound of formula I in an amount that is effective to prevent or delay the onset of type 2 diabetes mellitus.

Also included in a method of treating, preventing or delaying the onset of diseases or conditions that are associated with type 2 diabetes mellitus. Examples include diseases and conditions selected from the group consisting of: dyslipidemias, such as elevated levels of cholesterol, triglycerides or low density lipoproteins (LDL), low levels of high density lipoprotein (HDL), microvascular or macrovascular changes and the sequellae of such conditions, such as coronary heart disease, stroke, peripheral vascular disease, hypertension, renal hypertension, nephropathy, neuropathy and retinopathy. The method entails administering to a type 2 diabetic patient, e.g., a human patient, an amount of a compound of formula I that is effective for treating, preventing or delaying the onset of such diseases or conditions.

Optical Isomers—Diastereomers—Geometric Isomers—Tautomers

Many of the compounds of formula I contain one or more asymmetric centers and thus occur as racemates and racemic mixtures, single enantiomers, diastereomeric mixtures and individual diastereomers. The present invention includes all such isomeric forms of the compounds, in pure form as well as in mixtures.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixture thereof are encompassed with compounds of Formula I.

Salts and Solvates

The term "pharmaceutically acceptable salts" refers to salts prepared from pharmaceutically acceptable substantially non-toxic bases or acids including inorganic or organic bases and inorganic or organic acids, as well as salts that can be converted into pharmaceutically acceptable salts. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

Solvates as used herein refers to the compound of formula I or a salt thereof, in association with a solvent, such as water. Representative examples include hydrates, hemihydrates, trihydrates and the like.

References to the compounds of Formula I include the pharmaceutically acceptable salts and solvates.

This invention relates to method of antagonizing or inhibiting the production or activity of glucagon, thereby reducing the rate of gluconeogenesis and glycogenolysis, and the concentration of glucose in plasma.

The compounds of formula I can be used in the manufacture of a medicament for the prophylactic or therapeutic treatment of disease states in mammals caused by elevated levels of glucose.

Dose Rantes

The prophylactic or therapeutic dose of a compound of Formula I will, of course, vary with the nature of the condition to be treated, the particular compound selected and its route of administration. It will also vary according to the age, weight and response of the individual patient. In general, the daily dose range lie within the range of from about 0.001 mg to about 100 mg per kg body weight, preferably about 0.01 mg to about 50 mg per kg, and more preferably 0.1 to 10 mg per kg, in single or divided doses. It may be necessary to use dosages outside of these limits in some cases.

When intravenous or or oral administration is employed, a representative dosage range is from about 0.001 mg to about 100 mg (preferably from 0.01 mg to about 10 mg) of a compound of Formula I per kg of body weight per day, and more preferably, about 0.1 mg to about 10 mg of a compound of Formula I per kg of body weight per day.

Pharmaceutical Compositions

As mentioned above, the pharmaceutical composition comprises a compound of Formula I and a pharmaceutically acceptable carrier. The term "composition" encompasses a product comprising the active and inert ingredient(s), (pharmaceutically acceptable excipients) that make up the carrier, as well as any product which results, directly or indirectly, from the combination, complexation or aggregation of any two or more of the ingredients, or from dissociation of one or more of the ingredients, or from other types of reactions or interactions between ingredients. Preferably the composition is comprised of a compound of formula I in an amount that is effective to treat, prevent or delay the onset of type 2 diabetes mellitus, in combination with the pharmaceutically acceptable carrier.

Any suitable route of administration may be employed for providing a mammal, especially a human with an effective dosage of a compound of the present invention. For example, oral, rectal, topical, parenteral, ocular, pulmonary, nasal, and the like may be employed. Examples of dosage forms include tablets, troches, dispersions, suspensions, solutions, capsules, creams, ointments, aerosols and the like, with oral tablets being preferred.

In preparing oral compositions, any of the usual pharmaceutical media may be employed, such as, for example, water, glycols, oils, alcohols, flavoring agents, preservatives, coloring agents and the like in the case of oral liquids, e.g., suspensions, elixirs and solutions; or carriers such as starches, sugars, microcrystalline cellulose, diluents, granulating agents, lubricants, binders, disintegrating agents and the like in the case of oral solids, e.g., powders, capsules and tablets, with the solid oral preparations being preferred. Because of their ease of administration, tablets and capsules represent the most advantageous oral dosage unit forms. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 1 mg to about 1 g of the active ingredient and each cachet or capsule contains from about 1 to about 500 mg of the active ingredient.

The following are examples of pharmaceutical dosage forms for the compounds of Formula I:

The weight ratio of the compound of the Formula I to the second active ingredient may be varied within wide limits and depends upon the effective dope of each ingredient Generally, an effective dose of each will be used. Thus, for example, when a compound of the Formula I is combined with a PPAR agonist the weight ratio of the compound of the Formula I to the PPAR agonist will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

| Injectable Suspension (I.M.) | mg/mL | Tablet | mg/tablet |
|---|---|---|---|
| Compound of Formula I | 10 | Compound of Formula I | 25 |
| Methylcellulose | 5.0 | Microcrystalline Cellulose | 415 |
| Tween 80 | 0.5 | Povidone | 14.0 |
| Benzyl alcohol | 9.0 | Pregelatinized Starch | 43.5 |
| Benzalkonium chloride | 1.0 | Magnesium Stearate | 2.5 |
| Water for injection to make | 1.0 mL | Total | 500 mg |
| Capsule | mg/capsule | Aerosol | Per canister |
| Compound of Formula I | 25 | Compound of Formula I | 24 mg |
| Lactose Powder | 573.5 | Lecithin, NF Liq. Conc. | 1.2 mg |
| Magnesium Stearate | 1.5 | Trichlorofluoromethane, NF | 4.025 g |
| Total | 600 mg | Dichlorodifluoromethane, NF | 12.15 g |

Combination Therapy

Compounds of Formula I may be used in combination with other drugs that are used in the treatment/prevention/delaying the onset of type 2 diabetes mellitus, as well as the diseases and conditions associated with type 2 diabetes mellitus, for which compounds of Formula I are useful. Other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred Accordingly, the pharmaceutical compositions of the present invention include those that also contain one or more other active ingredients, in addition to a compound of Formula I Examples of other active ingredients that may be combined with a compound of Formula I either administered separately or in the same pharmaceutical compositions, include, but are not limited to: (a) bis-guanides (e.g., buformin, metformin, phenformin), (b) PPAR agonists (e.g., troglitazone, pioglitazone, rosiglitazone), (c) insulin, (d) somatostatin, (e) α-glucosidase inhibitors (e.g., voglibose, miglitol, acarbose), and (f) insulin secretagogues (e.g., acetohexamide, carbutamide, chlorpropamide, glibornuride, gliclazide, glimerpiride, glipizide, gliquidine, glisoxepid, glyburide, glyhexamide, glypinamide, phenbutamide, tolazamide, tolbutamide, tolcyclamide, nateglinide, repaglinide).

Throughout the instant application, the following abbreviations are used with the following meanings unless otherwise indicated:

| | |
|---|---|
| Bu = butyl | Bn = benzyl |
| BOC, Boc = t-butyloxycarbonyl | CBZ, Cbz = Benzyloxycarbonyl |
| DCC = Dicyclohexylcarbodiimide | DCM = dichloromethane |
| DIEA = diisopropylethylamine | DMF = N,-dimethylformamide |
| DMAP = 4-Dimethylaminopyridine | Et = ethyl |
| EtOAc = ethyl acetate | EtOH = ethanol |
| eq. = equivalent(s) | FAB-mass spectrum = Fast atom bombardment-mass spectroscopy |
| HOAc = acetic acid | HPLC = High pressure liquid chromatography |
| HOBT, HOBt = Hydroxybenztriazole | LAH = Lithium aluminum hydride |
| Me = methyl | PBS = phosphate buffer saline |
| Ph = phenyl | TFA = Trifluoroacetic acid |
| THF = Tetrahydrofuran | TMS = Trimethylsilane |

Compounds of the present invention may be prepared according to the methodology outlined in the following Schemes.

Scheme 1

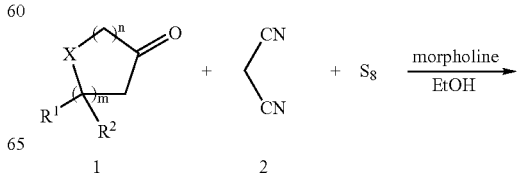

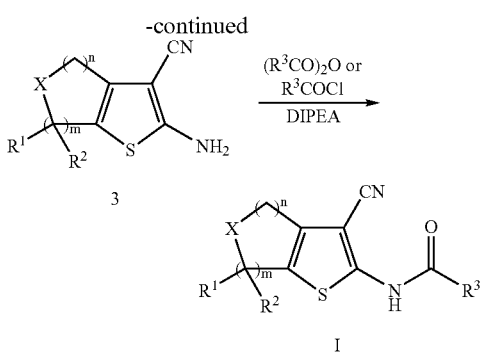

Cyclic ketones such as 1, where X is CR⁵R⁶ from formula I, are commercially available, known in the literature or may be conveniently prepared by a variety of methods familiar to those skilled in the art.

In Scheme 1, a cyclic ketone 1 is condensed with malonitrile 2 in the presence of sulfur ($S_8$) and a dialkylamine (e.g., morpholine) in ethanol according to methods described in the literature (S. Mukherjee and A. De, *J. Chem. Res.* 5, 295 (1994); M. S. Mahas et al. J. Chem. Soc. 1969, 1937; A. De et al. J. Het. Chem. 29, 1213 (1992)) to afford 2-amino-3-cyano-thiophene 3. Acylation of 3 with an appropriate anhydride or acid chloride in the presence of a trialkylamine (e.g., diisopropylethylamine) according to published procedues (U. Sensfuss et al. Heteroat. Chem. 9, 529 (1998) will afford the amide represented by formula I.

It is recognized that when the cyclic ketone 1 is not a symmetrically substituted ketone, the product 3 may be formed as a mixture of positional isomers. These isomers may be separated at any stage in the synthetic sequence by preparative thin layer chromatography, flash chromatography on silica gel as described by W. C. Still et al., *J. Org. Chem.*, 43, 2923 (1978), or HPLC. Compounds that are purified by HPLC may be isolated as the corresponding salt.

In some instances it may be necessary to carry out the thiophene synthesis in two steps, as illustrated in Scheme 2.

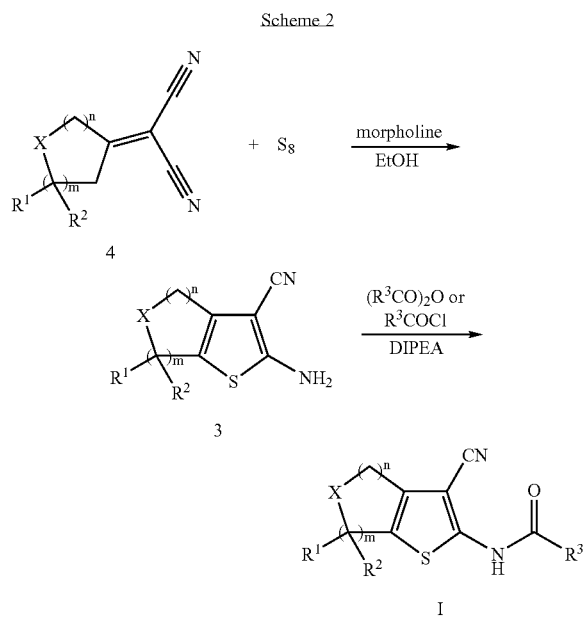

A dicyano-alkene 4 is first prepared by condensation of a ketone such as 1 and malonitrile. This intermediate is e d with sulfur ($S_8$) and a diallylamine (e.g., morpholine) in ethanol according to methods dearibed in the literature (A. Rajca and A Tisler, Monatch. Chem. 121, 697 (1990); B. Naumamn et al., Pharmazie 53, 4 (1996)) to afford 2-amino-3-cyanothiophene 3. Acylation of 3 with an appropriate anhydride or acid chloride in the presence of a trialkylamine (e.g., diisopropylethylamine) according to published procedures (U. Sensfuss et al. Heteroat. Chem. 9, 529 (1998) afford the thipheneamide represented by formula I.

Intermediates such as 5 in Scheme 3, where n is an integer greater than 0 and X is nitrogen are commercially available, known in the literature or may be prepared by a variety of known methods.

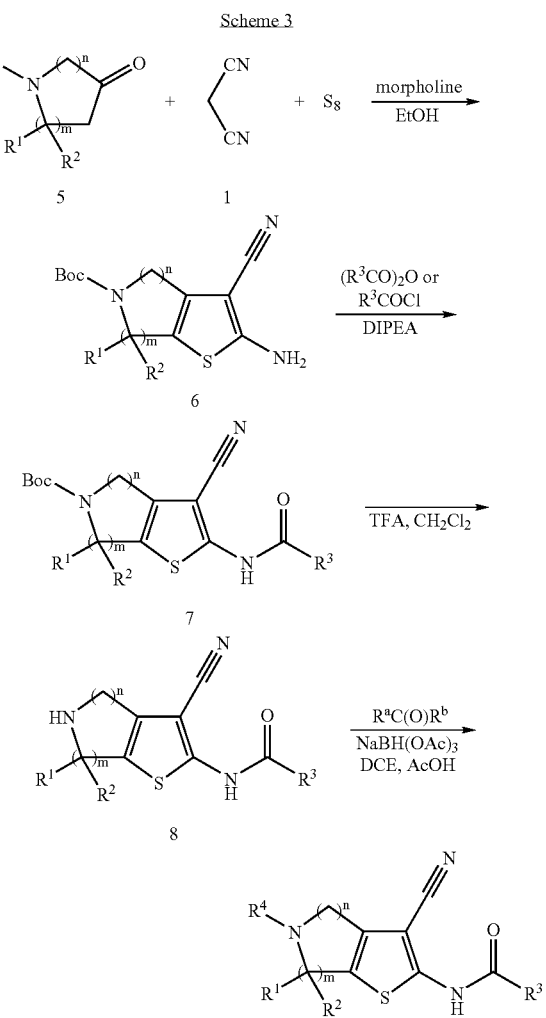

In the schemes, $R^a$, $R^b$ and $R^c$ are appended to reagents and can form part of a variable within the genus. Thus, for example, in scheme 3, the carbonyl attached to $R^a$ or $R^b$ and the variable am converted into $R^4$, and the other variable represents a suitable leaving group. In scheme 4, $R^c$ is converted into one of the moieties attached to the carbonyl group within $R^4$.

One route to compounds with the formula I using ketones is illustrated in Scheme 3. The intermediate 6 is obtained as illustrated in Scheme 1, followed by amide bond formation to afford the product of formula 7 as illustrated in Scheme 1. The intermediate 7 may be further elaborated by removal of the Boc protecting group with, for example, trifluoroacetic acid, to give the unprotected secondary amine 8. This amine may be further manipulated by the addition of a ketone $R^aCOR^b$ or aldehyde RCHO in a solvent such as 1,2-dichloroethane, in the presence of a mild acid, such as acetic acid, and a reducing agent, such as sodium triacetoxyborohydride, to form the alkylated amine 9.

The intermediate 8 may be otherwise manipulated by the method illustrated in Scheme 4.

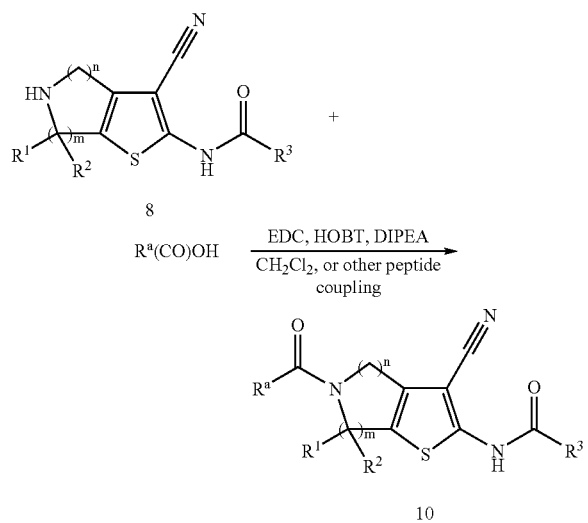

The amine 8 may be coupled to a carboxylic acid using 1-ethyl-3-(3-dimethylainopropyl)carbodiimide (EDC), 1-hydroxybenztriazole (HOBT), and a base, generally triethylamine or diisopropylethylamine (DIPEA), in a solvent such as N,N-dimethylformamide (DMF), tetrahydrofuran (THF), or methylene chloride for 3 to 48 hours at ambient temperature to provide intermediate 10.

Intermediates such as 11 may also be synthesized by the general method outline in Scheme I from the corresponding ketones, which are commercially available, known in the literature, or may be readily prepared by those familiar with the art. In some cases intermediate 11 may be deprotected using a mixture of aqueous hydrochloric acid and THF at 70° C. for 3 to 48 hours to afford the ketone intermediate 12, as illustrated in Scheme 5.

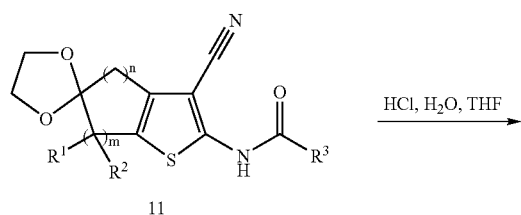

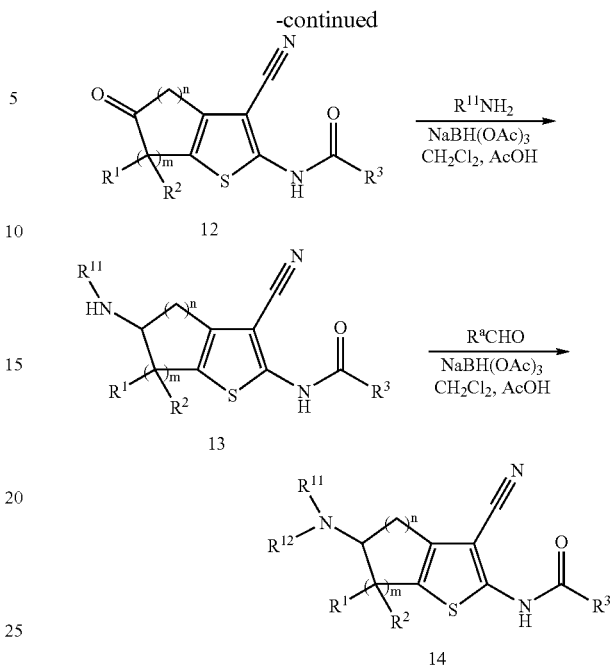

This intermediate may be further elaborated by the addition of a primary amine, such as $R^{11}NH_2$, in dichloromethane in the presence of a mild acid such as acetic acid, and a reducing agent such as sodium triacetoxyborohydride, to afford the amine product 13. This intermediate may be further elaborated by the addition of an aldeyde, also in the presence of a reducing agent and a mild acid, to form the tertiary amine product 14. $R^aCH$— from the aldehyde form the variable $R^{12}$ or a group that is readily converted to $R^{12}$.

The intermediate 13 may alternatively be manipulated as illustrated in Scheme 6, by the addition of a carboxylic acid $R^aC(O)OH$, using the peptide coupling conditions utilized in Scheme 4, or by the addition of an acid chloride, using the amide bond forming conditions utilized in Scheme 1. This affords the amide product 15.

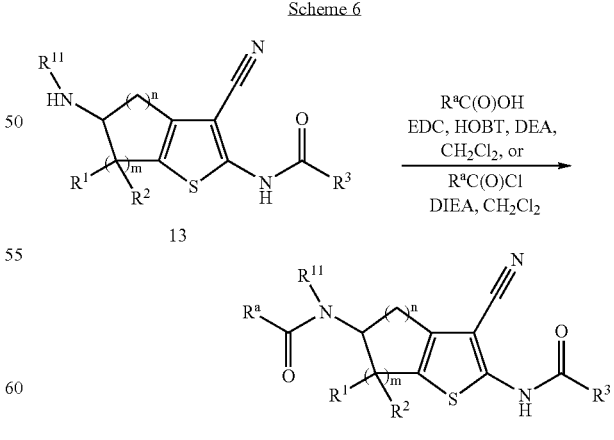

The following examples are illustrative of the present invention, and are not to be construed as limiting the scope of the appended claims.

EXAMPLE 1

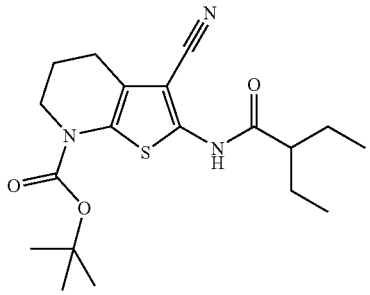

tert-Butyl 3-cyano-2-[(2-ethylbutanoyl)amino]-5,6-dihydrothieno[2,3-b]pyridine-7(4H)-carboxylate

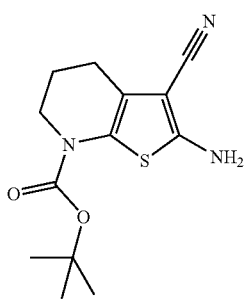

Step A. tert-Butyl 2-amino-3-cyano-5,6-dihydrothieno[2,3-b]pyridine-7(4H)-carboxylate The tide compound was prepared via the sequence outlined in Scheme 1. Thus, to 0.200 g (1.00 mmol) of tert-butyl 3-oxopiperidine-1-carboxylate in 20 mL of EtOH was added 0.066 g (1.00 mmol) of malononitrile, followed by 0.088 mL (1.00 mmol) of morpholine, then 0.032 g (1.00 mmol) of elemental sulfur. The mixture was stirred at ambient temp for 16 h, then diluted with an equal volume of saturated aqueous NaHCO$_3$. The mixture was extracted twice with dichloromethane, and the combined organic layers were dried (Na$_2$SO$_4$) and concentrated in vacuo. Purification by flash chromatography (20% EtOAc in hexane) afforded the tide compound as a white solid.

$^1$H NMR (500 MHz, CDCl$_3$) 4.62 (s, 2H), 3.73 (t, J=5.5 Hz, 2H), 2.56 (t, J=6.5 Hz, 2H), 1.98 (m, 2H), 1.52 (8, 9H); mass spectrum (ES) m/e=280.2 (M+H).

Step B. tert-Butyl 3-cyano-2[(2-ethylbutanoyl)amino]-5,6-dihydrothienol[2.3-b]pyridine-7(4H)-carboxylate To a solution of the material isolated in Step A in 1 mL of dichloromethane was added 0.200 mL (1.15 mmol) of di-iso-propylethylamine, followed by 0.100 mL (0.728 mmol) of 2-ethylbutanoyl chloride. After 16 hrs at ambient temperature the mixture was diluted with 30 mL of dichloromethane, then washed twice with an equal volume of saturated aqueous NaHCO$_3$. The organic layer was dried (Na$_2$SO$_4$) and concentrated in vacuo, affording the title compound.

$^1$H NM (500 MHz, CDCl$_3$) 8.88 (s, 1H), 3.75 (s, 2H), 2.62 (t, J=6.0 Hz, 2H), 2.30 (s, 1H), 1.99 (quint., J=5.5 Hz, 2H, 1.61 (m, 2H), 0.92 (t, J=7.0 Hz, 6H; mass spectrum (ES) m/e=378.2 (M+H).

EXAMPLE 2

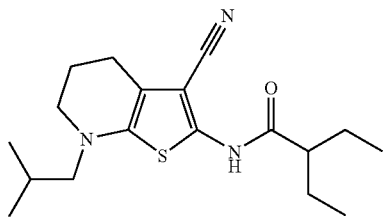

N-(3-Cyano-7-isobutyl-4,5,6,7-tetrahydrothieno[2,3-b]pyridin-2-yl)-2-ethylbutanamide

Step A. N-(3-Cyano-4,5,6,7-tetrahydrothieno[2-3-b]pyridin-2-yl)-2-ethylbutanamide To a solution of the tide compound from Example 1 in 20 mL of dichloromethane was added 20 mL of trifluoroacetic acid. After 1 h at ambient temperature, the mixture was concentrated in vacuo, and purified by flash chromatogaphy (40% EtOAc in hexane), affording the title compound.

$^1$H NMR (500 MHz, CDCl$_3$, TFA salt) 11.11 (s, 1H), 6.90 (s, 1H), 3.12 (s, 1H), 2.46 (m, 2H), 1.78 (t, J=5.5 Hz, 2H), 1.50 (m, 2H), 1.42 (m, 2H), 0.79 (t, J=7.5 Hz, 6H); mass spectrum (ES) m/e=278.2 (M+H).

Step B. N-(3-Cyano-7-isobutyl-4.5.6.7-tetrahydrothieno[2,3-b]pyridin-2-yl)-2-ethylbutanamide To the material isolated in Step A in 2 mL of dichloromethane was added 0.041 mL (0.90 mmol) of iso-butyraldehyde, followed by 0.026 mL (0.45 mmol) of acetic acid and 0.10 g (0.45 mmol) of sodium tracetoxyborohydride. After 16 h at ambient temperature the reaction was diluted with 30 mL of dichloromethane and washed twice with equal volumes of saturated aqueous NaHCO$_3$. The organic layer was dried (Na$_2$SO$_4$) and concentrated in vacuo. Purification by preparative reversed phase BPLC afforded the tide compound.

$^1$H NMR (TFA salt) (500 MHz, CDCl$_3$) 8.90 (s, 1H), 3.13 (t, J=5.5 Hz, 1H), 2.85 (d, J=7.5 Hz, 2H), 2.57 (t, J=6.5 Hz, 2H), 2.28 (m, 1H), 1.98 (m, 2H), 1.72 (m, 2H), 1.59 (m, 21), 0.94 (t, J=7.5 Hz, 6H), 0.93 (t, J=6.5 Hz, 6H); mass spectrum (ES) m/e=334 (M+1).

EXAMPLE 3

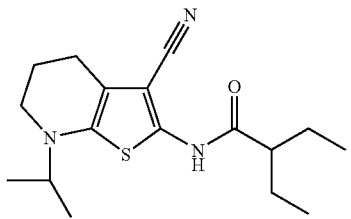

N-(3-Cyano-7-isopropyl-4,5,6,7-tetrahydrothieno[2,3-b]pyridin-2-yl)-2-ethylbutanamide The title compound was prepared in an identical manner to Example 2.

$^1$H NMR (TFA salt) (500 Mz, CDCl$_3$) 8.56 (s, 1H): 3.64 (quint, J=7.0 Hz, 1H), 3.07 (t, J=5.0 Hz, 2H), 2.57 (t, J=6.0 Hz, 2H), 2.46 (m, 1H), 1.97 (quint, J=5.5 Hz, 2H), 1.74 (m, 2H), 1.60 (m, 2H), 1.19 (d, J=7.0 Hz, 6H), 0.95 (t, J=7.5 Hz, 6H).

EXAMPLE 4

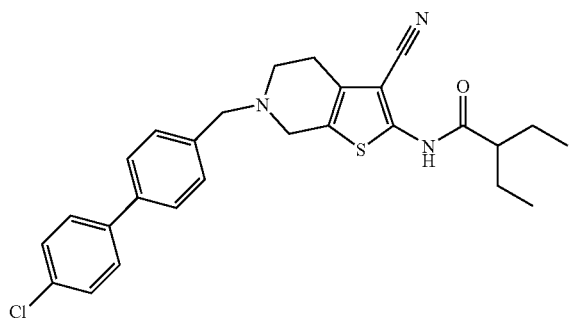

N-{6-[(4'-Chloro-1,1'-biphenyl-4-yl)methyl]-3-cyano-4,5,6,7-tetrahydrothieno [2,3-c]pyridin-2-yl}-2-ethylbutanamide

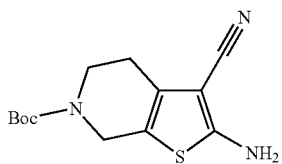

Step A. tert-Butyl 2-amino-3-cyano-4,7-dihythieno [2,3-c]pyridine-6-(5H)-carboxylate The title compound was prepared via the sequence outlined in Scheme 1. Thus, to 10.0 g (50.2 mmol) of tert-butyl 4-oxopiperidine-1-carboxylate in 150 mL of EtOH was added 3.3 g (50.2 mmol) of malononitrile, followed by 6.6 mL (75 mmol) of morpholine, then 1.61 g (50.2 mmol) of elemental sulfur. The mixture was stirred at ambient temperature for 16 h, then the reaction mixture was filtered through a pad of silica, washing with 50% EtOAc in hexane. The filtrate was concentrated in vacua, affording the title compound as a white solid.

$^1$H NMR (500 Mz, CDCl$_3$) 4.81 (s, 2H, 4.38 (s, 2H), 3.68 (t, J=5.0 Hz, 2H), 2.61 (s, 2H), 1.50 (s, 9H); mass spectrum (ES) m/e=180.2 (M+H-Boc).

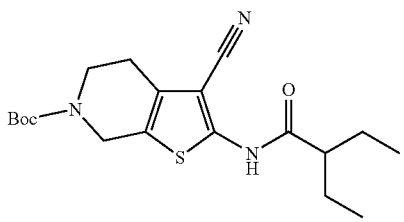

Step B. tert-Butyl 3-cyano-2-[(2-ethylbutanoyl)amino]-4,7-dihydrothieno[2,3-c]pyridine-6(5H)-carboxylate To a solution of 12.0 g (43.0 mmol) the intermediate prepared in Step A in 250 mL of dichloromethane was added 15.0 mL (86 mmol) of di-iso-propylamine, followed by 9.0 mL (64 mmol) of 2-ethylbutanoyl chloride. After 16 h at ambient temperature the reaction was diluted with an equal volume of saturated aqueous NaHCO$_3$, then extracted twice with dichloromethane. The combined organic layers were dried (Na$_2$SO$_4$) and concentrated in vacuo. Purification by flash chromatography (15% EtOAc in hexane) afforded the title compound as a white solid.

$^1$H NMR (500 MHz, CDCl$_3$) 9.23 (s, 1H), 4.50 (s, 2H), 3.71 (s, 2H), 2.69 (s, 2H), 2.35 (m, 1H), 1.76 (m, 2H), 1.63 (m, 2H), 1.50 (s, 9H), 0.95 (t, J=7.5 Hz, 6H); mass spectrum (BS) m/e=378.1 (M+H).

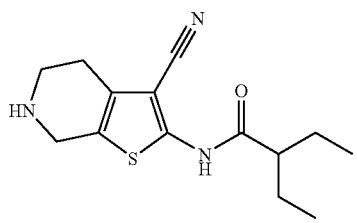

Step C. N-(3-Cyano-4,5,6,7-tetrahydrothieno[2,3-c]pyridin-2-yl)-2-ethylbutanamide To a solution of the intermediate isolated in Step B in 100 mL of dichloromethane was added 25 mL of trifluoroacetic acid. After 2 h at ambient temperature, the reaction was diluted with an equal volume of saturated aqueous NAHCO$_3$. The mixture was extracted twice with dichloromethane, and the combined organic layers were dried (Na$_2$SO$_4$) and concentrated in vacuo, affording the title compound.

$^1$H NMR (500 MHz, CDCl$_3$) 9.34 (s, 1H), 3.96 (s, 2H), 3.47 (s, 1H), 3.20 (t, J=5.5 Hz, 2H, 2.67 (t, J=6.0 Hz, 2H), 2.33 (m, 1H), 1.73 (m, 2H), 1.62 (m, 21p, 0.94 (s, 9H); mass spectrum (ES) m/e=278.2 (M+H).

Step D. N-{6-[(4'-Chloro-1,1'-biphenyl-4-yl)methyl]-3-cyano-4,5,6,7-tetrahydrothieno[2,3-c]pyridin-2-yl}-2-ethylbutanamide To a solution of the intermediate obtained in Step C in 2 mL of 1,2-dichloroethane was added 98.0 mg (0.45 mmol) of 4-(4-chlorophenyl)benzaldehyde, followed by 0.026 mL (0.45 mmol) of acetic acid, and 100 mg (0.45 mmol) of sodium triacetoxyborohydride. After 16 h at ambient temperature the reaction was diluted with an equal volume of saturated aqueous NaHCO$_3$, and the mixture was extracted twice with dichloromethane. The combined organic layers were dried (Na$_2$SO$_4$) and concentrated in vacuo. Purification by reversed phase preparative HPLC afforded the title compound as a white solid.

$^1$H NMR (TFA salt) (500 MHz, CDCl$_3$) 8.97 (s, 1H), 7.55 (m, 4H), 7.44 (m, 4H), 3.78 (s, 2H), 3.61 (s, 2H), 2.89 (t, J=5.5 Hz, 2H), 2.75 (t, J=5.5 Hz, 2H), 2.32 (m, 1H), 1.74 (m, 2H), 1.63 (m, 2H), 0.96 (t, J=7.0 Hz, 6H); mass spectrum (ES) m/e=478.2 (M+H).

EXAMPLE 5

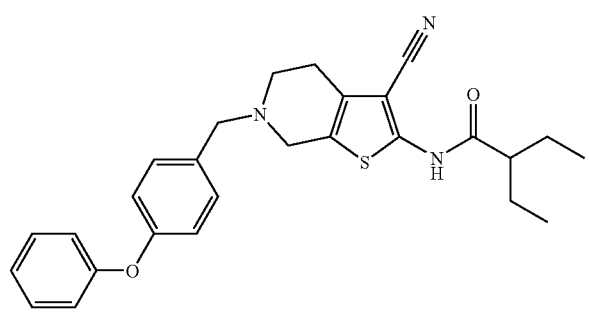

N-[3-Cyano-6-(4-phenoxybenzyl)-4,5,6,7-tetrahydrothieno[2,3-c]pyridin-2-yl]-2-ethylbutanamide The title compound was prepared in an identical manner to Example 4.

$^1$H NMR CIA salt) (500 MHz, CDCl$_3$) 9.26 (8, 1H), 7.35 (m, 4H), 7.13 (t, J=7.5 Hz, 1H), 7.04 (d, J=8.5 Hz, 2H), 7.01 (d, J=8.5 Hz, 2H), 3.71 (s, 2H), 3.58 (s, 2H), 2.86 (t, J=5.5 Hz, 2H, 2.74 (t, J=5.0 Hz, 2H), 2.37 (m, 1H), 1.75 (m, 2H), 1.62 (m, 2H), 0.96 (t, J=7.5 Hz, 6H); mass spectrum (ES) m/e=460.1 (M+H).

EXAMPLE 6

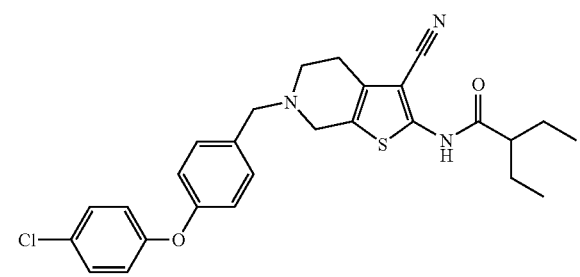

N-{6-[4-(4-Chlorophenoxy)benzyl]-3-cyano-4,5,6,7-tetrahydrothieno[2,3-c]pyridine-2-yl}-2-ethylbutanamide The title compound was prepared in an identical manner to Example 4.

$^1$H NMR (TFA salt) (500 Mhz, CDCl$_3$) 9.13 (s, 1H), 7.34 (t, J=8.0 Hz, 2H), 7.30 (d, J=8.5 Hz, 2H), 6.97 (d, J=8.5H, 2H), 6.96 (d, J=9.5 Hz, 2H), 3.70 (s, 2H), 3.57 (s, 2H), 2.85 (t, J=6.0 Hz, 2H), 2.72 (t, J=5.5 Hz, 2H), 2.33 (m, 1H), 1.75 (m, 2H), 1.61 (m, 2H), 0.94 (t, J=7.5 Hz, 6H); mass spectrum (ES) m/e=494.2 (M+H).

EXAMPLE 7

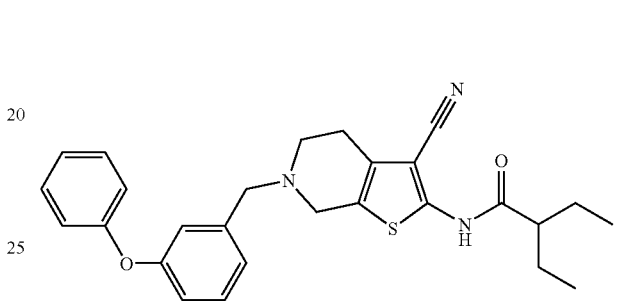

N-[3-Cyano-6-(3-phenoxybenzyl)-4,5,6,7-tetrahydrothieno[2,3-c]pyridine-2-yl]-2-ethylbutanamide The title compound was prepared in an identical manner to Example 4.

$^1$H NMR (TFA salt) (500 MHz, CDCl$_3$) 9.21 (s, 1H), 7.34 (m, 3H), 7.13 (d, J=7.5 Hz, 2H), 7.07 (s, 1H), 7.03 (d, J=8.0 Hz, 2H), 6.95 (d, J=8.0 Hz, 1H), 3.73 (s, 2H), 3.60 (s, 2H), 2.86 (t, J=5.0 Hz, 2H), 2.72 (t, J=4.5 Hz, 2H), 2.35 (m, 1H), 1.75 (m, 2H), 1.62 (m, 2H), 0.96 (t, J=7.5 Hz, 6H); mass spectrum (ES) m/e=460.1 (M+H).

EXAMPLE 8

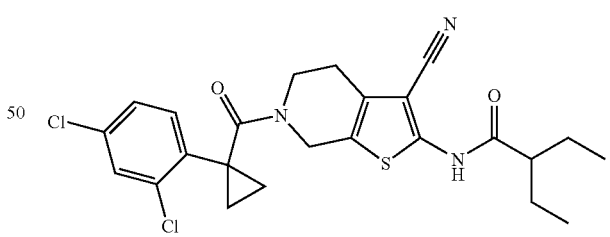

N-(3-Cyano-6-{[1-(2,4-dichlorophenyl)cylopropyl]carbonyl}-4,5,6,7-tetrahydrothieno[2,3-c]pyridin-2-yl)-2-ethylbutanamide To a solution of the intermediate prepared in Step C of Example 4 in 1 mL of DMP was added 4.2 mg (0.14 mmol) of 1-(2,4-dichlorophenyl)cyclopropanecarboxylic acid, followed by 0.047 mL (0.027 mmol) of di-isopropylethylamine and 68.0 mg (0.18 mmol) of O-(7-azabenzotriazol-1-yl)-N,N,N',N'-tetramehyluronium hexafluorophosphate (HATU).

After 16 h at ambient temperature the mixture was diluted with 50 mL of EtOAc. The organic layer was washed with saturated aqueous NaICO$_3$, and brine, dried (MgSO$_4$) and concentrated in vacuo. Purification by flash chromatography (30% EtOAc in hexane) afforded the tide compound as a white solid.

$^1$H NMR (500 MHz, CDCl$_3$) 8.69 (s, 1H), 7.38 (s, 1H), 7.29 (s, 2H), 4.46 (s, 2H), 3.71 (m, 2H), 2.26 (m, 1H), 1.74 (m, 2H), 1.68 (q, J=2.5 Hz, 2H), 1.62 (m, 2H), 1.16 (q, J=2.5 Hz, 2H), 0.93 (t, J=7.5 Hz, 6H); mass spectrum (ES) m/e=490.1 (M+H).

EXAMPLE 9

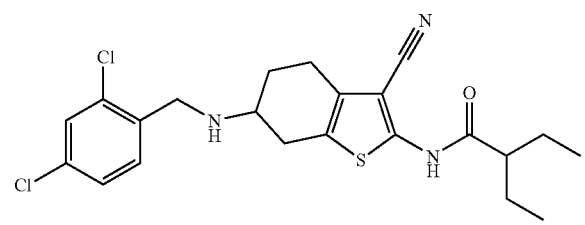

N-{3-Cyano-6[(2,4-dichlorobezyl)amino]-4,5,6,7-tetrahydro-1-benzothien-2-yl}-2-ethylbutanamide

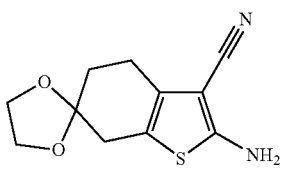

Step A. The title compound was prepared via the sequence outlined in Scheme 1. Thus, to 1,4-dioxaspiro(4.5]decan-8-one in 200 mL of EtOH was added 10.1 g (160 mmol) of malononitrile, followed by 22.0 mL (240 mmol) of morpholine, then 5.13 g (160 mmol) of elemental sulfur. The mixture heated to 100° C. for 16 h, then diluted with an equal volume of saturated aqueous NaHCO$_3$. The mixture was extracted twice with dichloromethane, and the combined organic layers were dried (Na$_2$SO$_4$) and concentrated in vacuo, affording a yellow solid.

Mass spectrum (ES) m/e=237.1 (M+H).

The crude material was carried directly on to Step B.

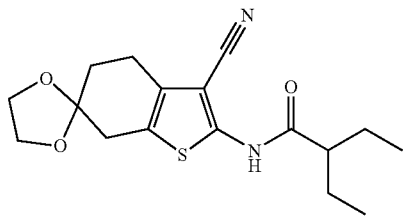

Step B. The crude material from Step A was dissolved in 200 mL of dichloromethane. To this solution was added 46.0 mL (263 mmol) of di-iso-propylethylamine, followed by 8.91 mL (66.0 mmol) of 2-ethylbutanoyl chloride. After 16 h at ambient temperature, the reaction was quenched with an equal volume of saturated aqueous NaHCO$_3$. The mixture was extracted twice with dichloromethane, and the combined organic layers were dried (Na$_2$SO$_4$) and concentrated in vacuo, affording a yellow solid.

Mass spectrum (ES) m/e=335.2 (M+H).

The crude material was carried directly on to Step C.

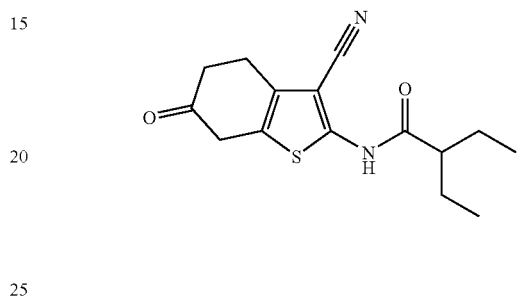

Step C. N-(3-Cyano-6-oxo-4,5,6,7-tetrahydro-1-benzothien-2-yl)-2-ethylbutanamide To the material isolated in Step B in 100 mL of THF was added 52 mL (52 mmol) of 1.0 N aqueous HCl. The mixture was heated to 70° C. for 48 h, then cooled to ambient temperature and added to 52 mL (52 mmol) of 1.0 N NaOH. The resulting mixture was extracted twice with dichloromethane, and the combined organic layers were dried (Na$_2$SO$_4$) and concentrated in vacuo. Purification by flash chromatography (20% EtOAc in hexane) afforded 0.650 g of the intermediate as a white solid.

$^1$H NMR (500 MHz, CDCl$_3$) 9.17 (s, 1H), 3.52 (s, 2H), 3.03 (t, J=6.5 Hz, 2H), 2.72 (t, J=8.0 Hz, 2H), 2.36 (m, 1H), 1.77 (m, 2H), 1.65 (m, 2H), 0.95 (t, J=7.5 Hz, 6H); mass spectrum (ES) m/e=291.2 (M+H).

Step D. N-{3-Cyano-6-[(2,4-dichlorobenzyl)amino]-4,5,6,7-tetrahydro-1-benzothien-2-yl}-2-ethylbutanamide To a solution of the intermediate isolated in Step C in 100 mL of dichloromethane was added 1.41 mL (12.0 mL) of 1-(2,4-dichlorophenyl)methanamine, followed by 2.54 g (12.0 mmol) of sodium triacetoxyborohydride, and 0.960 mL (16.0 mmol) of acetic acid. After 16 h at ambient temperature, the reaction was quenched with an equal volume of saturated aqueous NaHCO$_3$. The mixture was extracted twice with dichloromethane, and the combined organic layers were dried (Na$_2$SO$_4$), and concentrated in vacuo, affording a yellow solid. Purification by flash chromatography (15% EtOAc in hexane) afforded the title compound as a white solid.

$^1$H NMR (500 MHz, CDCl$_3$) 8.54 (s, 1H), 7.39 (m, 2H, 7.25 (m, 1H), 3.95 (s, 2H), 3.04 (m, 1H), 2.95 (dd, J=4.0 Hz, J=16.0 Hz, 1H), 2.78 (dt, J=5.5 Hz, J=16.5 Hz, 1H), 2.62 (m, 1H), 2.53 (dd, J=8.0 Hz, J=16.0 Hz, 1H), 2.25 (m, 1H), 2.09 (m, 1H), 1.76 (m, 2H), 1.64 (m, 2H), 1.56 (8, 1H), 0.95 (t, J=7.0 Hz); mas spectrum (ES) m/e=450.1 (M+H).

EXAMPLE 10

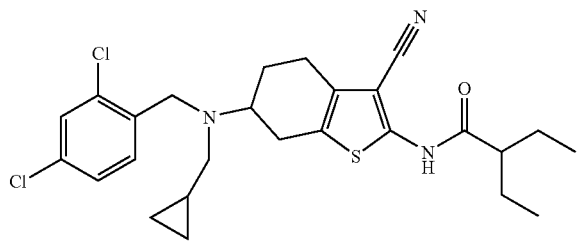

N-{3-Cyano-6-[cyclopropylmethyl)(2,4-dichlorobenzyl)amino]-4,5,6,7-tetrahydro-1-benzothien-2-yl}-2-ethylbutanamide To a solution of the title compound from Example 9 in 5 mL of dichloromethane was added 0.165 mL (2.20 mmol) of cyclopropanecarbaldehyde, followed by 0.187 g (0.88 mmol) of sodium triacetoxyborohydride. After 72 h at ambient temperature the mixture was diluted with an equal volume of saturated aqueous NaHCO$_3$, and extracted twice with dichloromethane. The combined organic layers were dried (Na$_2$SO$_4$) and concentrated in vacuo. Purification by flash chromatography, followed by purification by reversed phase preparative HPLC, afforded the title compound as a white solid.

$^1$H NMR (TFA salt) (500 MHz, CDCl$_3$) 8.28 (s, 1H), 7.74 (s, 1H), 7.38 (s, 1H), 7.29 (s, 1H), 3.99 (s, 2H), 2.91 (m, 1H), 2.85 (dd, J=7.0 Hz, J=17.0 Hz, 1H), 2.75 (m, 1H), 2.60 (m, 2H), 2.23 (m, 1H), 1.70 (m, 2H), 1.63 (m, 21), 0.95 (t, J=8.0 Hz, 6); mass spectrum (ES) m/e=504.1 (M+H).

Using the title compound prepared in Example 9, and following the procedure outlined in Example 10, the compounds listed in Table 3 were prepared.

TABLE 3

| Example | R$^{12}$ | Mass spectrum (ES) m/e = |
|---|---|---|
| 11 | isobutyl | 492.1 (M + H) |
| 12 | isohexyl (4-methylpentyl) | 520.2 (M + H) |
| 13 | 3,3-dimethylbutyl | 534.2 (M + H) |
| 14 | isobutyl variant | 506.2 (M + H) |
| 15 | 2-ethylbutyl | 534.2 (M + H) |
| 16 | (2,5-dimethylfuran-3-yl)methyl | 450.1 (M + H) |
| 17 | 3-phenylpropyl | 568.2 (M + H) |
| 18 | (benzofuran-2-yl)methyl | 580.2 (M + H) |
| 19 | 3,3-dimethylbutyl | 346.2 (M + H) |
| 20 | 4-fluorobenzyl | 558.1 (M + H) |
| 21 | (tetrahydrofuran-2-yl)methyl | 534.2 (M + H) |
| 22 | (5-methylfuran-2-yl)methyl | 544.2 (M + H) |
| 23 | (N-Boc-pyrrolidin-2-yl)methyl | 633.2 (M + H) |

Using the intermediate prepared in Example 9 Step C, and the procedure utilized in Example 9 Step D, the compounds listed in Table 4 were prepared.

TABLE 4

| Example | R⁵ | Mass spectrum (ES) m/e = |
|---|---|---|
| 24 | 3,4-dichlorobenzyl-NH- | 518.3 (M + H) |
| 25 | (2-phenylthiazol-5-yl)methyl-NH- | 465.3 (M + H) |
| 26 | (2-phenylthiazol-4-yl)methyl-NH- | 465.3 (M + H) |
| 27 | (1,2,3,4-tetrahydronaphthalen-1-yl)-NH- | 422.3 (M + H) |
| 28 | (indan-1-ylmethyl)-NH- | 422.3 (M + H) |
| 29 | 2-chlorobenzyl-NH- | 416.3 (M + H) |
| 30 | 1-(4-bromophenyl)ethyl-NH- | 476.2 (M + H) |
| 31 | 3-phenylpyrrolidin-1-yl- | 422.3 (M + H) |

TABLE 4-continued

| Example | R⁵ | Mass spectrum (ES) m/e = |
|---|---|---|
| 32 | 4-phenylpiperazin-1-yl- | 437.2 (M + H) |

EXAMPLE 33

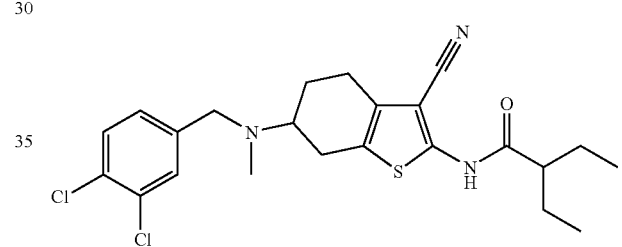

N-{3-Cyano-6-[(3,4-dichlorobenzyl)(methyl)amino]-4,5,6,7-tetrahydro-1-benzothien-2-yl}-2-ethylbutanamide To a solution of the title compound from Example 24 in 2 mL of dichloromethane was added 0.060 mL (0.65 mmol) of 37% aqueous formaldehyde, followed by 0.055 g (0.26 mmol) of sodium triacetoxyborohydride. After 16 h at ambient temperature, the reaction was diluted with 30 mL of dichloromethane and washed twice with an equal volume of saturated aqueous NaHCO₃. The organic layer was dried (Na₂SO₄) and concentrated in vacuo. Purification by preparative reversed phase HPLC afforded the title compound as a white solid (TFA salt).

¹H NMR (500 MHz, CDCl₃) 8.64 (s, 1H), 7.64 (m, 1H), 7.41 (m, 1H), 7.14 (d, J=8.0 Hz, 1H), 6.07 (s, 1H), 4.42 (d, J=5.5 Hz, 2H), 4.26 (m, 1H), 3.66 (m, 1H), 2.98 (m, 2H), 2.79 (s, 3H), 2.68 (m, 2H), 2.33 (m, 1H), 2.00 (m, 1H), 1.72 (m, 2H), 1.62 (m, 2H), 0.95 (t, J=8.0 Hz, 6H; mass spectrum (ES) m/e=464.2 (M+H).

Utilizing the procedure outlined in Example 33, and the title compound from the indicated Example as starting material, the compounds listed in Table 5 were prepared.

TABLE 5

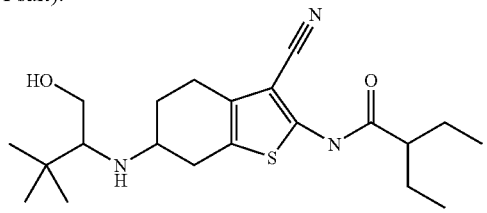

| Example | S. Mat. (Example) | R[11] | Mass Spectrum (ES) m/e = |
|---|---|---|---|
| 34 | 25 | (4-phenylthiazol-2-yl)methyl group | 479.3 (M + H) |
| 35 | 26 | (2-phenylthiazol-4-yl)methyl group | 479.3 (M + H) |
| 36 | 27 | 1,2,3,4-tetrahydronaphthalen-1-yl group | 436.3 (M + H) |
| 37 | 28 | 2,3-dihydro-1H-inden-1-yl group | 436.3 (M + H) |
| 38 | 29 | 2-chlorobenzyl group | 430.3 (M + H) |
| 39 | 30 | 1-(4-bromophenyl)ethyl group | 490.2 (M + H) |

EXAMPLE 40

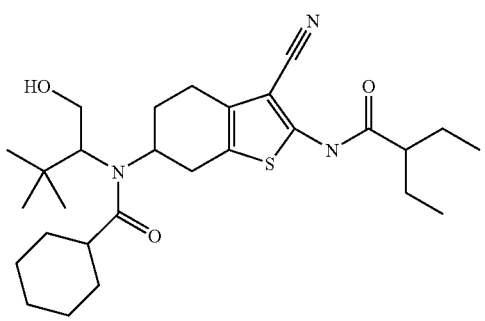

N-{3-Cyano-2-[(2-ethylbutanoyl)amino]-4,5,6,7-tetrahydro-1-benzothien-6-yl}-N-[1-hydroxymethyl)-2,2-dimethylpropyl]cyclohexanecarboxamide Step A. N-(3-Cyano-6-{[1-(hydroxymethyl)-2,2-dimethylpropyl]amino}-4,5,6,7-tetrahydro-1-benzothien-2-yl)-2-ethylbutanamide To a solution of the intermediate isolated in Example 9, Step C, in 40 mL of dichloromethane was added 0.452 g (3.90 mmol) of 2-amino-3,3-dimethylbutan-1-ol, followed by 1.24 g (5.9 mmol) of sodium triacetoxyborohydride and 0.468 mL (7.80 mmol) of acetic acid. After 16 h at ambient temperature the reaction was diluted with an equal volume of saturated aqueous NaHCO₃. The organic layer was dried (Na₂SO₄) and concentrated in vacuo. Purification by preparative reversed phase HPLC afforded the title compound (TFA salt).

Mass spectrum (ES) m/e=392.3 (M+H).

Step B. N-{3-Cyano-2-[(2-ethylbutanoyl)amino]-4,5,6,7-tetrahydro-1-benzothien-6-yl}-N-[1-(hydroxymethyl)-2,2-dimethylpropyl]cyclohexanecarboxamide To a solution of the intermediate isolated in Step A in 5.0 mL of dichloromethane was added 0.175 mL (1.00 mmol) of di-isopropylethylamine and 0.041 mL (0.280 mmol) of cyclohexanecarbonyl chloride. After stirring 16 h at ambient temperate, the reaction mixture was concentrated in vacuo, and purified by preparative reversed phase HPLC, affording the title compound as a white solid.

$^1$H NMR (500 MHz, CDCl₃) 8.51 (s, 1H), 4.52 (dt, J=3.5 Hz, J=12.5 Hz, 1H), 4.42 (dd, J=7.5 Hz, J=13.0 Hz, 1H), 3.75 (m, 1H), 3.08 (m, 2H), 2.88 (m, 1H), 2.67 (m, 1H), 2.51 (m, 1H), 2.27 (m, 3H), 2.18 (m, 1H), 1.86 (d, J=11.0 Hz, 1H), 1.76 (m, 3H), 1.62 (m, 2H), 1.40 (m, 1H), 1.27 (m, 1H), 1.20 (s, 9H), 0.95 (t, J=7.0 Hz); mass spectrum (ES) m/e=502.4 (M+H).

Utilizing the procedure outlined in Example 40 Step B, and the starting material synthesized in Example 40, Step A, the compounds listed in Table 6 were synthesized.

TABLE 6

| Example | R[12] | Mass spectrum (ES) m/e = |
|---|---|---|
| 41 | cyclopropanecarbonyl group | 460.3 (M + H) |

TABLE 6-continued

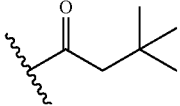

| Example | R[12] | Mass spectrum (ES) m/e = |
|---|---|---|
| 42 | 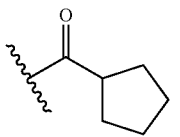 | 490.4 (M + H) |
| 43 | 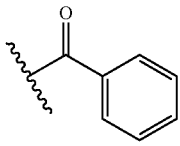 | 488.4 (M + H) |
| 44 | 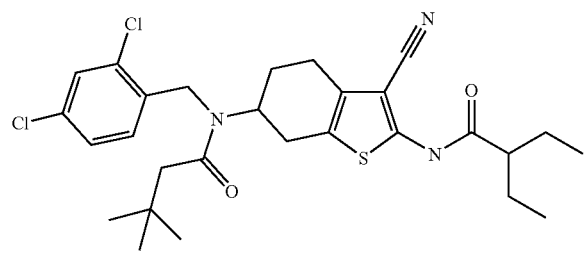 | 496.4 (M + H) |

EXAMPLE 45

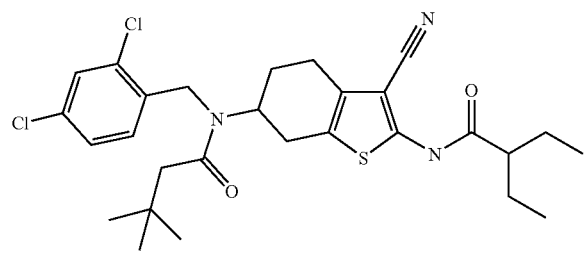

N-{3-Cyano-2-[(2-ethylbutanoyl)amino]-4,5,6,7-tetrahydro-1-benzothien-6-yl}-N-(2,4-dichlorobenzyl)-3,3-dimethylbutanamide To a solution of the title compound from Example 9 in 50 mL of dichloromethane was added 0.307 mL (1.80 mmol) of di-iso-propylethylamine, a catalytic amount (ca. 2 mg) of HOBT, and 0.065 mL (0.48 mmol) of 3,3-ethylbutanoyl chloride. After 16 h at ambient temperature the read on was diluted with an equal volume of saturated aqueous NaHCO$_3$. The organic layer was dried (NSO$_4$) and concentrated in vacuo. Purification by preparative reversed phase HPLC afforded the title compound as a white solid.

$^1$HNMR (300 MHz, CDCl$_3$) 8.52 (s, 1H), 7.46 (s, 1H), 7.34 (m, 1H), 7.20 (m, 1H), 4.97 (m, 1 μl), 4.72 (d, J=17 Hz, 1H), 4.59 (d, J=16 Hz, 1H), 2.73 (m, 4H), 2.25 (m, 1H), 2.12 (s, 2H), 1.86 (m, 2H), 1.78 (m, 2H), 1.60 (m, 2H), 1.07 (s, 9H), 0.94 (t, J=7.5 Hz, 6H); mass spectrum (ES) m/e=548.1 (M+H).

Biological Assays

The ability of the compounds of the present invention to inhibit the binding of glucagon can be demonstrated using the following in vitro assays.

Glucapon Receptor Binding Assay

A stable CHO (Chinese hamster Ovary) cell line expressing cloned human glucagon receptor was maintained as described (Chicchi et al. *J Biol Chem* 272, 7765-9(1997); Cascieri et al. *J Biol Chem* 274, 8694-7(1999)). To determine antagonistic binding affinity of compounds 0.002 mg of cell membranes from these cells were incubated with $^{125}$I-Glucagon (New England Nuclear, MA) in a buffer containing 50 mM Tris-HCl (pH 7.5), 5 mM MgCl$_2$, 2 mM EDTA, 12% Glycerol, and 0.200 mg WGA coated PVT SPA beads (Amersham), +/− compounds or 0.001 mM unlabeled glucagon. After 412 hours incubation at room temperature, the radioactivity bound to the cell membranes was determined in a radioactive emission detection counter (Mcro-beta-Wallace). Data was analyzed using the software program Prisms from GraphPad. The IC$_{50}$ were calculated using non-linear regression analysis assuming single site competition.

High Throughput Screening (HTS) Protocol for Glucagon Receptor Binding Assay

Another form of the binding assay was developed suitable for high-throughput screening for modulators of receptor activity. Fully automated or semi-automated protocols and robotic and workstation instruments were utilized for the HTS assay as would be recognized by those practiced in the art. In a typical configuration of the assay, 0.002 mg of cell membrane (as described above) were preincubated with 0.200 mg of WGA-coated PVT beads in buffer containing 100 mM Tris-HCl pH 7.5, 10 mM MgCl$_2$, 4 mM EDTA, 24% Glycerol, and 0.2% BSA. The membrane/bead mixture was then dispensed (0.050 mL) into each well of 96-well plates (Wallac Isoplates, white clear bottom) containing 0.100 mL of test compounds or control solutions. A second addition (0.050 mL) was then dispensed into the wells of the plate containing $^{125}$I-Glucagon (approximately 25,000 CPM). The solutions were dispensed using a Multidrop Stacker 20 (Titertek) liquid dispenser. An adhesive plate seal (Packard) was applied and the plates were shaken for 5 minutes. The plates were further incubated at ambient temperature for several hours for establishment of equilibrium (typically 5 hours) and the signal was stable for up to three days. The plates were read in a scintillation counter (Wallac Microbeta) for 1 min/well. Activity of test compounds was calculated by comparing to the total scintillation signal (CPM) of control samples with no compound and with 0.001 mM unlabeled-glucagon.

Inhibition of Glucagon-stimulated Intracellular cAMP Formation

Exponentially growing CHO cells expressing human glucagon receptor were harvested with the aid of enzyme-free dissociation media (Specialty Media), pelleted at low speed, and re-suspended in cell suspension buffer [75 mM Tris-HCl pH 7.5, 250 mM Sucrose, 25 mM MgCl$_2$, 1.5 mM EDTA, 0.1 mM Ro-20-1724 (Biomol, Inc.), 0.2% bovine serum albumin and one tablet of complete™ (Boehringer), which contains a cocktail of protease inhibitors, for each 50 ml of buffer]. An adenylate cyclase assay was setup using an Adenylate Cyclase Assay kit (SMP-004B) from New England Nuclear (NEN) as per manufacturer instructions. Briefly, compounds were diluted from stocks in a cell stimulation buffer supplied with the kit. Cells prepared as above were preincubated in flash plates coated with anti-cAMP antibodies (NEN) in presence of compounds or DMSO controls for 40 minutes, and then stimulated with glucagon (250 pM) for an additional 40 minutes. The cell stimulation was stopped by addition of equal amount of a detection buffer containing lysis buffer as well as $^{125}$I-labeled cAMP tracer (NEN). After 3-6 h of incubation at room temperature the bound radioactivity was determined in a liquid scintillation counter TopCount-Packard Instruments). Activity of test compounds was calculated by comparing to the total scintillation signal (CPM) of control samples with no compound and with 0.001 mM unlabeled-glucagon.

Certain embodiments of the invention has been described in detail; however, numerous other embodiments are contemplated as falling within the invention. Thus, the claims are not limited to the specific embodiments described herein. All patents, patent applications and publications that are cited herein are hereby incorporated by reference in their entirety.

What is claims is:

1. A compound represented by formula I:

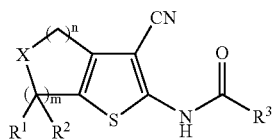

or a pharmaceutically acceptable salt or solvate thereof wherein:

X is $NR^4$;

$R^1$ is selected from the group consisting of: H, $C_{1-10}$alkyl, $C_{3-7}$cycloalkyl and Aryl, said alkyl, cycloalkyl and Aryl being optionally substituted with 1-4 substituents independently selected from $R^{13}$;

$R^2$ is selected from the group consisting of: $R^1$ as defined above, —C(O)$_2$R$^7$ and —CONR$^7$R$^8$;

m is 0;

n is 3;

$R^3$ is selected from the group consisting of: $C_{1-10}$alkyl, $C_{3-7}$cycloalkyl and Aryl, said alkyl, cycloalkyl and Aryl being optionally substituted with 1-4 substituents selected from $R^{13}$, such that when $R^3$ represents $C_{1-10}$ alkyl substituted with one $R^{13}$ group, and $R^{13}$ represents halo, $R^1$, $R^2$, $R^5$ and $R^6$ do not represent $C_{1-3}$alkyl;

$R^4$ is selected from the group consisting of: $C_{3-10}$ alkyl, $C_{3-7}$ cycloalkyl, Aryl, HAR, Hetcy, C(O)C$_{5-10}$ alkyl, C(O)C$_{3-7}$ cycloalkyl, C(O)-Aryl, C(O)-HAR, C(O)-Hetcy, CONR$^9$R$^{10}$, CO$_2$R$^9$ and SO$_2$R$^9$, the alkyl, cycloalkyl, Aryl, HAR and Hetcy groups and portions being optionally substituted with 1-4 substituents selected from $R^{13}$;

one of $R^5$ and $R^6$ is selected from the group consisting of NR$^{11}$R$^{12}$, NR$^{11}$COR$^{12}$, NR$^{11}$CO$_2$R$^{12}$ and NR$^{11}$S(O)$_2$R$^{12}$, and the other represents $R^1$, HAR, Hetcy or OR$^{11}$, said HAR and Hetcy being optionally substituted with 1-4 substituents selected from $R^{13}$, $R^7$, $R^{10}$ and $R^{11}$ are selected from the group consisting of: $R^1$ as defined above, HAR and Hetcy, said HAR and Hetcy being optionally substituted with 1-4 substituents selected from $R^{13}$;

$R^8$, $R^9$ and $R^{12}$ are selected from the group consisting of: $C_{1-10}$alkyl, $C_{3-7}$cycloalkyl, Aryl, HAR and Hetcy, said alkyl, cycloalkyl, Aryl, HAR and Hetcy being optionally substituted with 1-4 substituents selected from $R^{13}$;

or alternatively, $R^7$, $R^8$, $R^9$ and $R^{10}$ are as defined above, and $R^{11}$ and $R^{12}$ are taken together with the atoms to which they are attached along with any intervening atoms and represent a 5-8 membered ring optionally containing 1-2 heteroatoms selected from O, S and N, and optionally substituted with 1-4 substituents selected from $R^{13}$;

each $R^{13}$ is selected from the group consisting of: halo, NR$^{14}$R$^{15}$, $C_{1-4}$alkyl, $C_{3-7}$ cycloalkyl, Aryl, HAR, Hetcy, CF$_3$, OCF$_3$, OR$^{15}$, NO$_2$, S(O)$_x$R$^{14}$, SR$^{14}$, S(O)$_x$NR$^{14}$R$^{15}$, O(CR$^{16}$R$^{17}$)$_y$NR$^{14}$R$^{15}$, C(O)R$^{14}$, CO$_2$R$^{15}$, CO$_2$(CR$^{16}$R$^{17}$)yCONR$^{14}$R$^{15}$, OC(O)R$^{14}$, CN, C(O)NR$^{14}$R$^{15}$, NR$^{15}$C(O)R$^{14}$, NR$^{15}$C(O)OR$^{14}$, NR$^{15}$C(O)NR$^{16}$R$^{14}$ and CR$^{15}$(N—OR$^{14}$), wherein x is 1 or 2, and y is an integer from 1-4, said alkyl, cycloalkyl, Aryl, HAR and Hetcy being optionally substituted with 1-4 substituents selected from $R^{18}$;

$R^{14}$, $R^{15}$, $R^{16}$ and $R^{17}$ are independently selected from the group consisting of: H, $C_{1-10}$alkyl, $C_{3-7}$cycloalkyl, Aryl and Ar—$C_{1-10}$alkyl;

and each $R^{18}$ is independently selected from the group consisting of: halogen, CN, $C_{1-4}$alkyl, OH, CF$_3$, Aryl, Aryloxy, CO$_2$H and CO$_2$C$_{1-4}$ alkyl, said Aryl and the Aryl portion of Aryloxy being optionally substituted with up to 4 halo groups, and up to 2 $C_{1-4}$ alkyl, OH, CF$_3$ or CN groups.

2. A compound in accordance with claim 1 wherein $R^1$ is selected from the group consisting of: H, $C_{1-10}$alkyl, $C_{3-6}$ cycloalkyl and phenyl, said alkyl and phenyl being optionally substituted with 1-3 substituents selected from $R^{13}$.

3. A compound in accordance with claim 1 wherein $R^2$ is H.

4. A compound in accordance with claim 1 wherein $R^3$ is $C_{3-10}$ alkyl optionally substituted with 1-4 substituents selected from $R^{13}$, such that when $R^3$ is substituted with one $R^{13}$ group, and $R^{13}$ represents halo, $R^1$, $R^2$, $R^1$ and $R^6$ do not represent $C_{1-3}$alkyl.

5. A compound in accordance with claim 4 wherein $R^3$ represents $C_{3-5}$ alkyl, optionally substituted with 1-4 $R^{13}$ groups.

6. A compound in accordance with claim 1 wherein $R^4$ is selected from the group consisting of: $C_5s_{10}$ alkyl, $C_{3-6}$ cycloalkyl, phenyl, HAR, Hetcy, C(O)C$_{5-10}$alkyl, C(O)C$_{3-6}$ cycloalkyl and CO$_2^9$, the alkyl, cycloalkyl and, Aryl groups and portions, phenyl, HAR and Hetcy being optionally substituted with 1-4 substituents selected from $R^{13}$, and $R^9$ representing $C_{1-10}$alkyl, $C_{3-7}$cycloalkyl, Aryl, HAR or Hetcy, said alkyl, cycloalkyl, Aryl groups and portions, HAR and Hetcy being optionally substituted with 1-4 $R^{13}$ groups.

7. A compound in accordance with claim 1 wherein $R^{13}$ is selected from the group consisting of: halo, $C_{1-4}$alkyl, $C_{3-7}$cycloalkyl, Aryl, HAR, Hetcy, and OR$^{15}$ wherein $R^{15}$ is H, said alkyl, cycloalkyl, Aryl, HAR and Hetcy being optionally substituted with 1-4 substituents selected from $R^{18}$ and $R^{18}$ is halo, $C_{1-4}$alkyl, Aryl or CO$_2$C$_{1-4}$ alkyl.

8. A compound in accordance with claim 1 selected from the group consisting of: tert-butyl 3-cyano-2-[(2-ethylbutanoyl)amino]-5,6-dihydrothieno[2,3-b]pyridine-7(4H) carboxylate; N-(3-cyano-7-isobutyl-4,5,6,7-tetrahydrothieno[2,3-b]pyridin-2-yl)-2-ethylbutanamide; and N-(3-cyano-7-isopropyl-4,5,6,7-tetrahydrothieno[2,3-b]pyridin-2-yl)-2-ethylbutanamide.

9. A pharmaceutical composition which is comprised of a compound in accordance with claim 1 in combination with a pharmaceutically acceptable carrier.

10. A method of treating type 2 diabetes mellitus in a mammalian patient in need of such treatment, comprising administering to said patient a compound in accordance with claim 1 in an amount that is effective to treat type 2 diabetes mellitus.

* * * * *